(12) United States Patent
Davoudi et al.

(10) Patent No.: US 9,173,735 B2
(45) Date of Patent: *Nov. 3, 2015

(54) POROUS URETERAL STENT

(71) Applicant: Boston Scientific Scimed, Inc., Maple Grove, MN (US)

(72) Inventors: Hamid Davoudi, Westwood, MA (US); Alfred P. Intoccia, Jr., Nashua, NH (US); Jianmin Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/282,959

(22) Filed: May 20, 2014

(65) Prior Publication Data

US 2014/0257511 A1    Sep. 11, 2014

Related U.S. Application Data

(63) Continuation of application No. 13/488,075, filed on Jun. 4, 2012, now Pat. No. 8,740,989, which is a continuation of application No. 12/567,367, filed on Sep. 25, 2009, now Pat. No. 8,414,656.

(60) Provisional application No. 61/120,109, filed on Dec. 5, 2008.

(51) Int. Cl.
*A61F 2/04* (2013.01)
*A61M 25/00* (2006.01)
*A61M 27/00* (2006.01)

(52) U.S. Cl.
CPC .................. *A61F 2/04* (2013.01); *A61M 25/00* (2013.01); *A61M 27/008* (2013.01); *A61F 2002/048* (2013.01)

(58) Field of Classification Search
CPC ................ A61F 2/04; A61F 2/06; A61F 2/07
USPC ........................... 623/1, 15–1.48, 1.15–1.48, 623/23.64–23.67
See application file for complete search history.

(56) References Cited

U.S. PATENT DOCUMENTS 5,129,910 A    7/1992    Phan et al.
6,395,021 B1    5/2002    Hart et al.
(Continued)

FOREIGN PATENT DOCUMENTS

DE    10155767 A1    5/2003
EP    0672394 A1    9/1995
(Continued)

OTHER PUBLICATIONS

Non-Final Office Action received for U.S. Appl. No. 13/488,075, mailed on Aug. 21, 2013, 6 pages.
(Continued)

*Primary Examiner* — Suzette J Gherbi
(74) *Attorney, Agent, or Firm* — Kacvinsky Daisak Bluni PLLC

(57) ABSTRACT

In some embodiments, a stent includes an elongate member and a distal retention member. The elongate member is configured to be disposed within a ureter of a patient and has a first portion, a second portion and a plurality of beads bonded together. The plurality of beads define a plurality of spaces between the plurality of beads. The plurality of spaces are configured to allow fluid to flow from the first portion of the elongate member to the second portion of the elongate member. The distal retention member is configured to help maintain a portion of the stent within a kidney of the patient.

12 Claims, 17 Drawing Sheets

(56) References Cited

U.S. PATENT DOCUMENTS

| | | |
|---|---|---|
| 7,041,139 B2 | 5/2006 | Bluni et al. |
| 7,491,234 B2 | 2/2009 | Palasis et al. |
| 7,862,552 B2 | 1/2011 | McIntyre et al. |
| 7,931,683 B2 | 4/2011 | Weber et al. |
| 8,029,554 B2 | 10/2011 | Holman et al. |
| 8,414,656 B2 | 4/2013 | Davoudi et al. |
| 8,740,989 B2 * | 6/2014 | Davoudi et al. ............ 623/23.66 |
| 2008/0124373 A1 | 5/2008 | Xiao et al. |
| 2008/0160259 A1 | 7/2008 | Nielson et al. |
| 2009/0138076 A1 | 5/2009 | Palasis et al. |
| 2009/0187254 A1 | 7/2009 | Deal et al. |
| 2009/0248169 A1 | 10/2009 | Li |
| 2009/0317766 A1 | 12/2009 | Heidenau et al. |
| 2009/0319032 A1 | 12/2009 | Weber et al. |
| 2010/0008970 A1* | 1/2010 | O'Brien et al. ............... 424/426 |
| 2010/0057197 A1* | 3/2010 | Weber et al. ................ 623/1.42 |
| 2010/0070022 A1* | 3/2010 | Kuehling .................... 623/1.16 |
| 2010/0145467 A1* | 6/2010 | Davoudi et al. ............. 623/23.7 |
| 2010/0241219 A1* | 9/2010 | Willard et al. ............... 623/1.42 |
| 2011/0112629 A1 | 5/2011 | Pathak |
| 2011/0118818 A1 | 5/2011 | Masters et al. |
| 2011/0184531 A1* | 7/2011 | Goraltchouk et al. ..... 623/23.72 |
| 2012/0303133 A1 | 11/2012 | Davoudi et al. |

FOREIGN PATENT DOCUMENTS

| | | | |
|---|---|---|---|
| WO | 99/09911 A2 | 3/1999 | |
| WO | 2010/065187 A2 | 6/2010 | |
| WO | 2010/065187 A3 | 10/2010 | |

OTHER PUBLICATIONS

Response to Non-Final Office Action for U.S. Appl. No. 13/488,075, filed Nov. 12, 2013, 6 pages.
Notice of Allowance received for U.S. Appl. No. 13/488,075, mailed on Jan. 21, 2014, 5 pages.
International Search Report and Written Opinion received for PCT Patent Application No. PCT/US2009/059784, mailed on Aug. 31, 2010, 18 pages.
International Preliminary Report on Patentability received for PCT Patent Application No. PCT/US2009/059784, mailed on Jun. 16, 2011, 10 pages.
Non-Final Office Action received for U.S. Appl. No. 12/567,367, mailed on Nov. 15, 2011, 8 pages.
Response to Non-Final Office Action for U.S. Appl. No. 12/567,367, filed Feb. 14, 2012, 7 pages.
Notice of Allowance received for U.S. Appl. No. 12/567,367, mailed on Mar. 5, 2012, 5 pages.
Non-Final Office Action received for U.S. Appl. No. 12/567,367, mailed on Jul. 20, 2012, 7 pages.
Response to Non-Final Office Action for U.S. Appl. No. 12/567,367, filed Sep. 27, 2012, 7 pages.
Supplemental Notice of Allowance received for U.S. Appl. No. 12/567,367, mailed on Dec. 12, 2012, 5 pages.

* cited by examiner

POROUS URETERAL STENT

CROSS-REFERENCE TO RELATED APPLICATIONS

This application is a continuation of, and claims priority to, U.S. patent application Ser. No. 13/488,075, filed on Jun. 4, 2012, entitled "POROUS URETERAL STENT", which is a continuation of U.S. patent application Ser. No. 12/567,367, filed on Sep. 25, 2009, entitled "POROUS URETERAL STENT", now U.S. Pat. No. 8,414,656, which claims priority to U.S. Provisional Patent Application No. 61/120,109, filed on Dec. 5, 2008, entitled "POROUS URETERAL STENT", the disclosures of which are hereby incorporated by reference in their entirety.

BACKGROUND

The invention relates generally to a medical implant and more particularly to a stent configured to be implanted within a ureter of a patient.

A ureter is a tubular passageway in a body that carries urine from a kidney to a bladder. Ureteral stents are used to assist drainage of urine and/or other fluids from the kidney to the urinary bladder in patients with a ureteral obstruction and/or injury; or to protect the integrity of the ureter during a variety of surgical manipulations. Stents may be used to treat and/or avoid ureteral obstructions (such as ureteral stones or ureteral tumors), which disrupt the flow of urine from the kidneys to the bladder. Serious obstructions may cause urine to back up into the kidneys. Ureteral stents may also be used after endoscopic inspection of the ureter to prevent obstruction of the ureter by swelling of the ureteral wall caused by the surgical procedure. Ureteral stents typically are tubular in shape and terminate in two opposing ends: a kidney-end and a bladder-end.

Known stents, typically include a lumen extending through a tubular passageway. Such known stents, however, do not allow for maximum drainage from the kidney to the bladder. Additionally, known stents are typically rigid to allow for easy placement in a ureter of a patient. Such rigidity, however, can cause patient discomfort and can make the stent more difficult to remove.

A need exists for a stent that provides increased drainage of urine from the kidney to the bladder of a patient. Further, a need exists for a stent that is sufficiently rigid when inserted but causes less patient discomfort after implementation and is easily removable.

SUMMARY

In some embodiments, a stent includes an elongate member and a distal retention member. The elongate member is configured to be disposed within a ureter of a patient and has a first portion, a second portion and a plurality of beads bonded together. The plurality of beads define a plurality of spaces between the plurality of beads. The plurality of spaces are configured to allow fluid to flow from the first portion of the elongate member to the second portion of the elongate member. The distal retention member is configured to help maintain a portion of the stent within a kidney of the patient. In some embodiments, the elongate member defines a longitudinal axis and the plurality of spaces are configured to allow fluid to flow in a direction substantially normal to the longitudinal axis.

BRIEF DESCRIPTION OF THE DRAWINGS

FIG. 9b is a side view of the bead of FIG. 9a.

DETAILED DESCRIPTION

In some embodiments, a stent includes an elongate member and a distal retention member. The elongate member is configured to be disposed within a ureter of a patient and has a first portion, a second portion and a plurality of beads bonded together. The plurality of beads define a plurality of spaces between the plurality of beads. The plurality of spaces are configured to allow fluid to flow from the first portion of the elongate member to the second portion of the elongate member. The distal retention member is configured to help maintain a portion of the stent within a kidney of the patient.

In some embodiments, a stent includes an elongate member having a distal end portion, a proximal end portion and a plurality of beads. The elongate member defines a longitudinal axis. Each bead of the plurality of beads has a first portion and a second portion. The first portion of each bead of the plurality of beads defines a lumen. The lumens of the first portion of each bead of the plurality of beads are substantially aligned along the longitudinal axis such that the lumen defined by the first portion of a first bead of the plurality of beads is disposed adjacent to and is in fluid communication with the lumen defined by the first portion of a second bead of the plurality of beads. The second portion of the first bead of the plurality of beads is offset from the second portion of the second bead of the plurality of beads.

In some embodiments, a stent includes an elongate member configured to extend from a kidney to a bladder of a patient. The elongate member includes a first material and a second material. The second material is interspersed within the first material and is configured to dissolve when the stent is disposed within a urinary tract of the patient for a predetermined amount of time. In such an embodiment, the stent is softer after the second material dissolves.

The words "proximal" and "distal" refer to direction closer to and away from, respectively, an operator (e.g., surgeon, physician, nurse, technician, etc.) who would insert the stent into the patient. Thus, for example, the end of the stent first inserted inside the patient's body would be the distal end of the stent, while the end of the stent to enter the patient's body last would be the proximal end of the stent.

Figure 1:
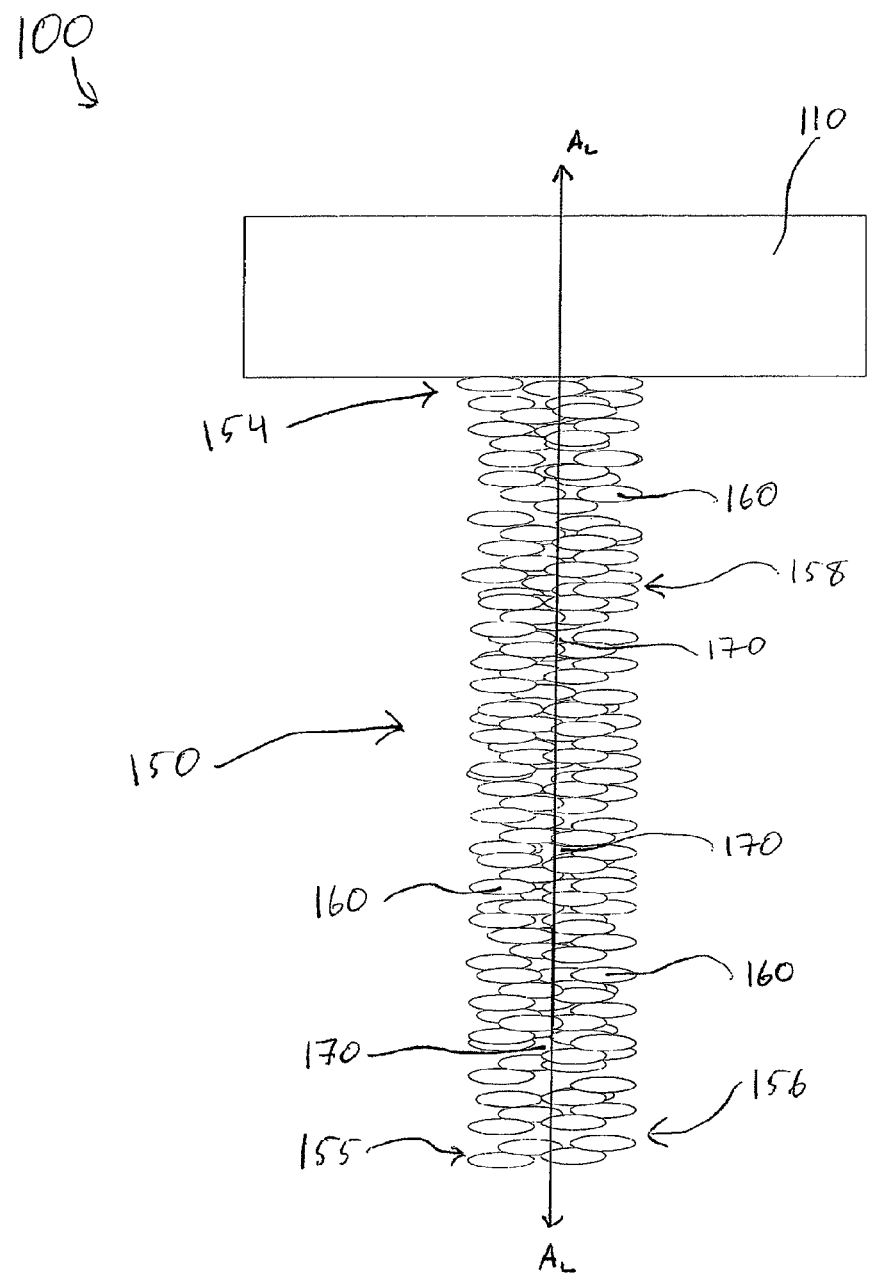
FIG. 1 is a schematic illustration of a stent according to an embodiment.

FIG. 1 is a schematic illustration of a stent 100 according to an embodiment. Stent 100 includes a retention member 110 and an elongate member 150. The elongate member 150 of the stent 100 defines a longitudinal axis $A_L$. The elongate member 150 of the stent 100 includes a distal end portion 154, a proximal end portion 155, a first portion 158, a second portion 156 and a plurality of beads 160 that define a plurality of spaces 170. The elongate member 150 of the stent 100 is configured to be disposed within a ureter of a patient. In some embodiments, the stent 100 is configured to provide support to the ureter of the patient. In some embodiments, the first portion 158 of the elongate member 150 is located at the distal end portion 154 of the elongate member 150. In some embodiments, the second portion 156 of the elongate member 150 is located at the proximal end portion 155 of the elongate member 150.

Each bead of the plurality of beads 160 can be any suitable shape. In some embodiments, the plurality of beads 160 are substantially spherical, figure-eight shaped, and/or the like. In some embodiments, each bead of the plurality of beads 160 has a relatively large surface area with rounded corners. The relatively large surface area of each bead of the plurality of beads 160 increases the area defined by the plurality of spaces 170 between the plurality of beads 160, as further described herein. The rounded corners of the beads reduces the irritation and/or damage the stent 100 can potentially cause to the ureter of the patient.

The plurality of beads 160 can be constructed of any suitable biocompatible material. In some embodiments, the plurality of beads 160 are constructed of thermal elastic plastic.

Each bead of the plurality of beads 160 is configured to be coupled to adjacent beads of the plurality of beads 160. In this manner, the plurality of beads 160 are coupled together to form the elongate member 150. The elongate member 150 is substantially cylindrical. In other embodiments, the plurality of beads can be coupled together to form an elongate member of any suitable shape.

Each bead of the plurality of beads 160 can be coupled to adjacent beads of the plurality of beads 160 by any suitable means. In some embodiments, each bead of the plurality of beads 160 is melted to adjacent beads. In other embodiments, each bead of the plurality of beads is coupled to adjacent beads by an adhesive, a weld, or the like.

The plurality of beads 160 are coupled to each other such that a plurality of spaces 170 are defined between the plurality of beads 160. The plurality of spaces 170 are configured to allow fluid to flow in a direction substantially parallel to the longitudinal axis $A_L$ from the first portion 158 of the elongate member 150 to the second portion 156 of the elongate member 150, as described in further detail herein. Further, the plurality of spaces 170 are configured to allow fluid to flow in a direction substantially normal to the longitudinal axis $A_L$. Thus, the stent has little resistance to urine flow between the plurality of spaces 170 of the elongate member 150 and the area surrounding the elongate member 150.

The retention member 110 of the stent 100 is coupled to the distal end portion 154 of the elongate member 150 and is configured to help retain a portion of the stent 100 in a kidney of a patient when the stent 100 is placed within a urinary tract of a patient. The retention member 110 is also configured to help prevent the proximal migration of the stent 100 when the stent 100 is placed within the urinary tract of the patient with the retention member 110 disposed in the kidney of the patient. In this manner, the retention member 110 is configured to help retain the elongate member 150 in a ureter of the patient.

The retention member 110 can be any shape sufficient to prevent the proximal migration of the stent 100 when placed within the urinary tract of the patient. The retention member 110 can be, for example, an elongate member coiled in a pigtail or J-shape. In other embodiments, the retention member includes protrusions coupled to the distal end portion of the elongate member that extend in a direction substantially normal to the longitudinal axis $A_L$. In still other embodiments, the retention member includes a malicot coupled to the distal end portion of the elongate member.

In some embodiments, the stent includes a second retention member similar to the retention member 110. The second retention member can be coupled to the proximal end portion of the elongate member. In some embodiments, the second retention member is disposed within the bladder of the patient when the stent is placed within the urinary tract of the patient. In this manner, the second retention member can help prevent distal migration of the stent when the stent is placed within the urinary tract of the patient with the second retention member disposed in the bladder.

In use, the stent 100 is inserted into the urinary tract of a patient. In some embodiments, the stent 100 can be inserted into the urinary tract using a delivery sheath or the like. The stent 100 is placed within the urinary tract such that the retention member 110 is disposed within the kidney of the patient and the elongate member 150 extends from the kidney of the patient to the bladder of the patient. When urine is in the kidney of the patient, the urine can flow through the plurality of spaces 170 defined by the plurality of beads 160 from the first portion 158 of the elongate member 150 to the second portion 156 of the elongate member 150 and into the bladder of the patient.

While FIG. 1 shows the entire elongate member 150 constructed of a plurality of beads 160, in some embodiments, only a portion of the elongate member is constructed of a plurality of beads. For example, in some embodiments, the distal end portion and/or the proximal end portion of the stent can be solid. Said another way, the distal end portion and/or the proximal end portion of the stent can be devoid of a plurality of lumens.

In some embodiments, some and/or all of the plurality of beads include a therapeutic agent. The therapeutic agent can be configured to promote wound healing when the stent is disposed adjacent a wound. In some embodiments, the therapeutic agent is configured to dissolve and enter the urine stream when the stent is disposed within the urinary tract of a patient. In this manner, the therapeutic agent can promote wound healing and/or induce other desired effects on a portion of a body of a patient that is not directly in contact with the elongate member. In other embodiments, some and/or all of the plurality of beads are configured to generate oxygen when exposed to the urine of a patient.

Figure 2:
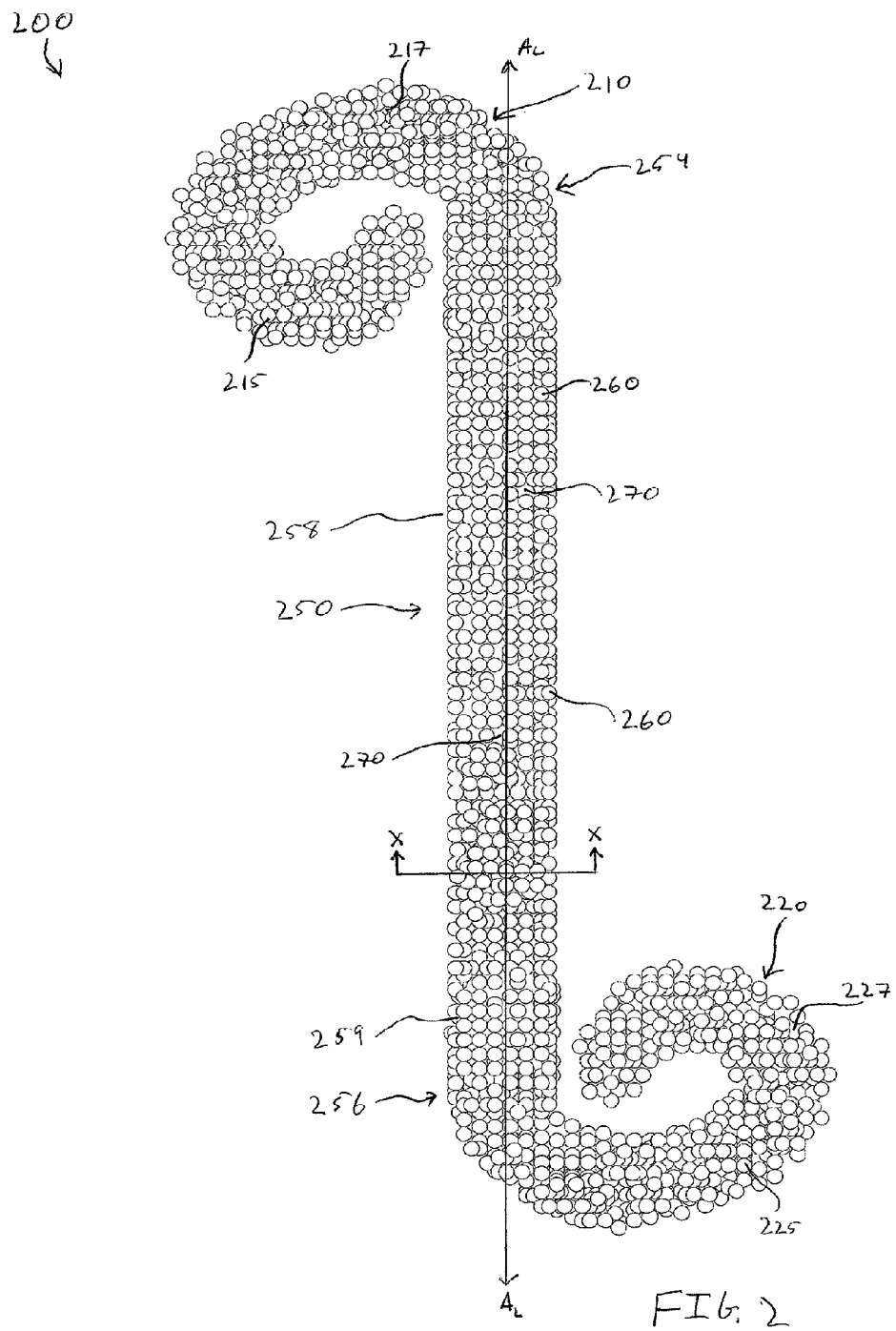
FIG. 2 is a front view of a stent according to an embodiment.
Figure 3:
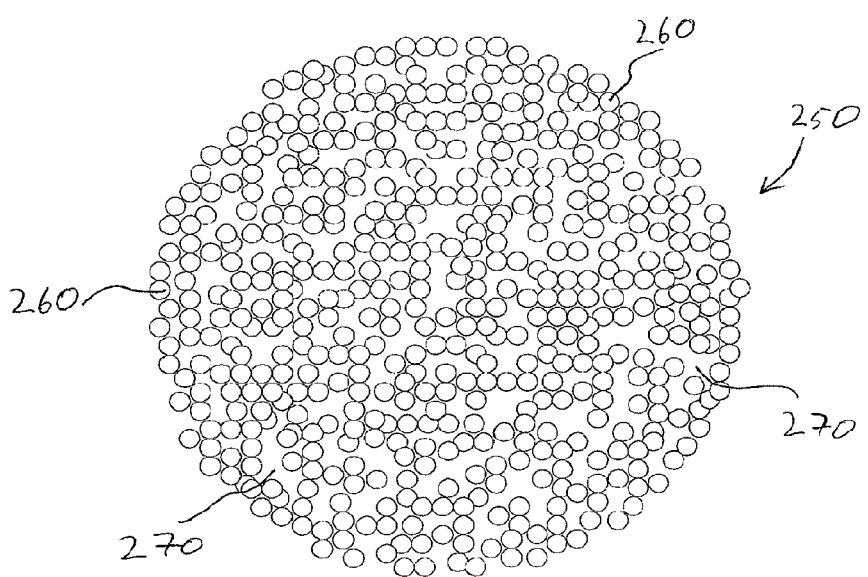
FIG. 3 is a cross-sectional view of the stent shown in FIG. 2, taken along line X-X in FIG. 2.

FIGS. 2 and 3 show a stent 200 according to an embodiment. Stent 200 includes a distal retention member 210, a proximal retention member 220 and an elongate member 250. The elongate member 250 of the stent 200 defines a longitudinal axis A1. The elongate member 250 of the stent 200 includes a first portion 258, a second portion 259, a distal end portion 254, a proximal end portion 256 and a plurality of beads 260 that define a plurality of spaces 270. The elongate member 250 of the stent 200 is configured to be disposed within a ureter of a patient. In some embodiments, the elongate member 250 is configured to provide support to the ureter of the patient. In some embodiments, the first portion 258 of the elongate member 250 is located at the distal end portion 254 of the elongate member 250, and the second portion 259 of the elongate member 250 is located at the proximal end portion 256 of the elongate member 250.

Each bead of the plurality of beads 260 is spherically shaped. Because the plurality of beads 260 are spherically shaped, each bead of the plurality of beads 260 has a relatively large surface area and does not include sharp corners. The relatively large surface area of the plurality of beads 260 increases the size of the plurality of spaces 270 between the plurality of beads 260. Additionally, the rounded corners of the plurality of beads 260 reduces the irritation and/or damage the stent 200 can potentially cause to the ureter of the patient.

The plurality of beads 260 can be constructed of any suitable biocompatible material. In some embodiments, for example, the plurality of beads 260 can be constructed of a thermal elastic plastic.

Each bead of the plurality of beads 260 is configured to be coupled to adjacent beads of the plurality of beads 260. In this manner, the plurality of beads 260 are coupled together to form the elongate member 250. The elongate member 250 is substantially cylindrical. In other embodiments, the plurality of beads are coupled together to form an elongate member of any suitable shape.

Each bead of the plurality of beads 260 can be coupled to adjacent beads of the plurality of beads 260 by any suitable means. In some embodiments, each bead of the plurality of beads 260 is melted to adjacent beads. In other embodiments, each bead of the plurality of beads is coupled to adjacent beads by an adhesive, a weld, and/or the like.

The plurality of beads 260 are coupled to each other such that the plurality of spaces 270 are defined between the plurality of beads 260. The plurality of spaces 270 are configured to allow fluid to flow in a direction substantially parallel to the longitudinal axis $A_L$ from the first portion 258 of the elongate member 250 to the second portion 259 of the elongate member 250, as described in further detail herein. Further, the plurality of spaces 270 are configured to allow fluid to flow in a direction substantially normal to the longitudinal axis $A_L$. Thus the stent has little resistance to urine flow between the plurality of spaces 270 of the elongate member 250 and the area surrounding the elongate member 250.

The distal retention member 210 is coupled to the distal end portion 254 of the elongate member 250 and includes a plurality of beads 215 structurally and functionally similar to the plurality of beads 260 of the elongate member 250. Each bead of the plurality of beads 215 is spherically shaped and configured to be coupled to adjacent beads of the plurality of beads 215. In this manner, the plurality of beads 215 are coupled together to form the distal retention member 210.

The plurality of beads 215 of the distal retention member 210 are coupled to each other such that a plurality of spaces 217 are defined between the plurality of beads 215. The plurality of spaces 217 are configured to allow fluid to flow between the plurality of beads 215. This allows fluid to flow between the kidney and the elongate member 250 when the stent 200 is disposed within the urinary tract of the patient.

The distal retention member 210 has a pigtail shape. The pigtail shape of the distal retention member 210 is configured to help retain a portion of the stent 200 in a kidney of a patient when the stent 200 is placed within a urinary tract of a patient. The distal retention member 210 is configured to help prevent proximal migration of the stent 200 when the stent 200 is disposed within the urinary tract of the patient with the distal retention member 210 disposed in the kidney of the patient. In this manner, the distal retention member 210 is configured to help retain the elongate member 250 in a ureter of a patient.

While the distal retention member 210 is shown having a pigtail shape, the distal retention member 210 can be any shape sufficient to prevent the proximal migration of the stent 200 when placed within the urinary tract of the patient. In some embodiments, the distal retention member is an elongate member coiled in a J-shape. In other embodiments, the distal retention member includes protrusions coupled to the distal end portion of the elongate member that extend in a direction substantially normal to the longitudinal axis $A_L$. In still other embodiments, the distal retention member includes a malicot coupled to the distal end portion of the elongate member.

The proximal retention member 220 is coupled to the proximal end portion 254 of the elongate member 250 and includes a plurality of beads 225 structurally and functionally similar to the plurality of beads 260 of the elongate member 250 and the plurality of beads 215 of the distal retention member 210. Each bead of the plurality of beads 225 is spherically shaped and configured to be coupled to adjacent beads of the plurality of beads 225. In this manner, the plurality of beads 225 are coupled together to form the proximal retention member 220.

The plurality of beads 225 of the proximal retention member 220 are coupled to each other such that a plurality of spaces 227 are defined between the plurality of beads 225. The plurality of spaces 227 are configured to allow fluid to flow between the plurality of beads 225. This allows fluid to flow between the elongate member 250 and a bladder of a patent when the stent 200 is disposed within the ureteral tract of a patient.

The proximal retention member 220 has a pigtail shape. The pigtail shape of the proximal retention member 220 is configured to help retain a portion of the stent 200 in a bladder of a patient when the stent 200 is placed within a urinary tract of a patient. The proximal retention member 220 is configured to prevent distal migration of the stent 200 when the stent 200 is placed within the urinary tract of the patient with the proximal retention member 220 disposed in the kidney of the patient. In this manner, the proximal retention member 220 is configured to help retain the elongate member 250 in a ureter of a patient.

While the proximal retention member 220 is shown having a pigtail shape, the proximal retention member 220 can be any shape sufficient to prevent the distal migration of the stent 200 when placed within the urinary tract of the patient. In some embodiments, the proximal retention member is an elongate member coiled in a J-shape. In other embodiments, the proximal retention member includes protrusions coupled to the proximal end portion of the elongate member that extend in a direction substantially normal to the longitudinal axis $A_L$. In still other embodiments, the proximal retention member includes a malicot coupled to the proximal end portion of the elongate member.

In use, the stent 200 is inserted into the urinary tract of a patient. In some embodiments, the stent 200 is inserted into the urinary tract using a delivery sheath or the like. The stent 200 is placed within the urinary tract such that the distal retention member 210 is disposed within the kidney of the patient, the proximal retention member 220 is disposed within the bladder of the patient, and the elongate member 250 extends from the kidney of the patient to the bladder of the patient. When urine is in the kidney of the patient, the urine can flow through the plurality of spaces 270 defined by the plurality of beads 260 from the first portion 258 of the elongate member 250 to the second portion 259 of the elongate member 250 and into the bladder of the patient.

Figure 6:
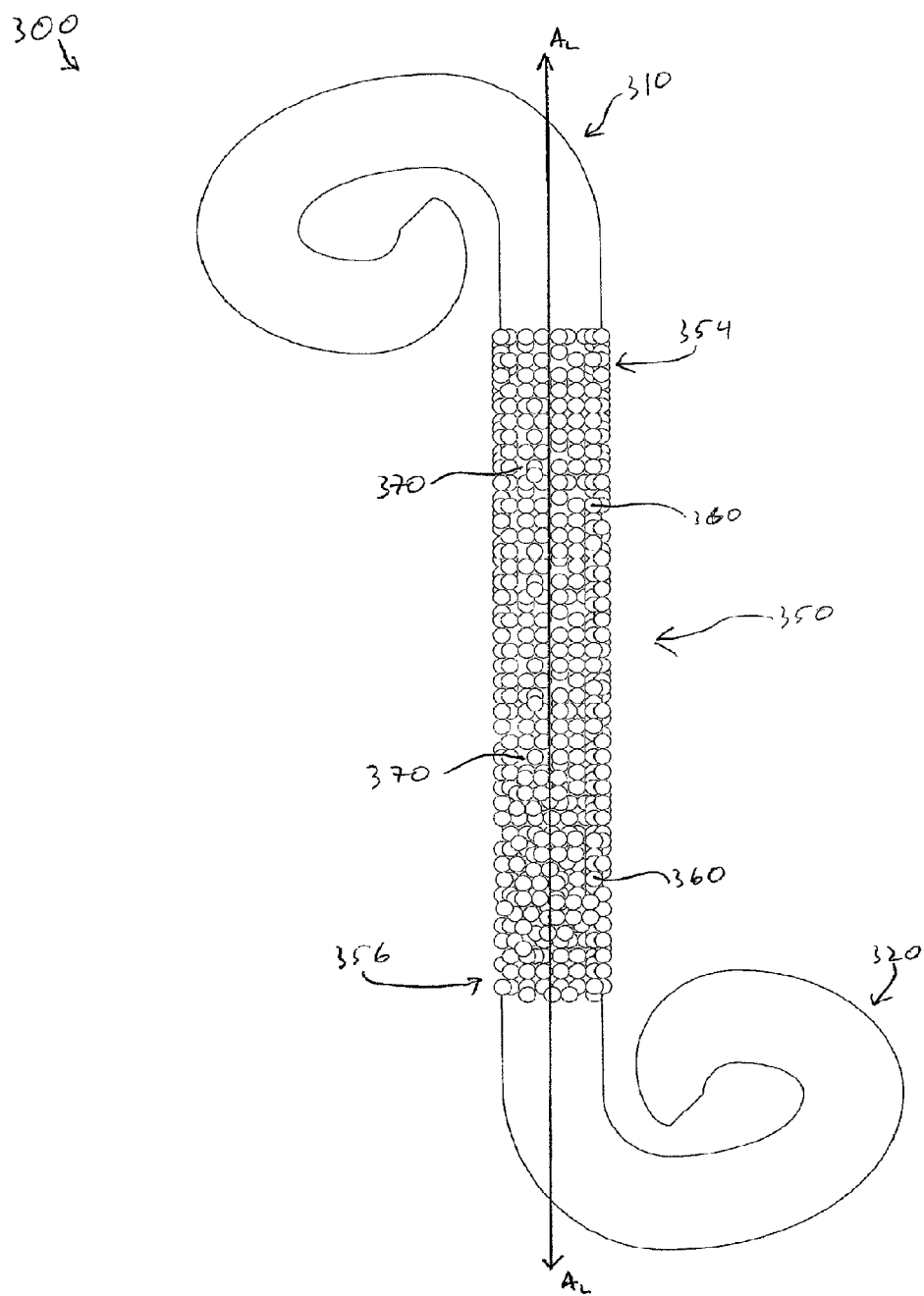
FIG. 6 is a front view of a stent according to an embodiment.

While FIG. 2 shows the entire stent 200 constructed of beads, in some embodiments, only a portion of a stent is constructed of beads. For example, FIG. 6 shows a stent 300 having an elongate member 350 constructed of a plurality of beads 360, a solid distal retention member 310 and a solid proximal retention member 320. The stent 300 is similar to the stent 200.

The plurality of beads 370 of the stent 300 are coupled together and define a plurality of spaces 370 between them. The plurality of spaces 370 are configured to allow fluid to flow in a direction substantially parallel to a longitudinal axis $A_L$ from a distal end portion 354 of the elongate member 350 to a proximal end portion 356 of the elongate member 350. Further, the plurality of spaces 370 are configured to allow fluid to flow in a direction substantially normal to the longitudinal axis $A_L$. Thus, there is little resistance to urine flow between the plurality of spaces 370 of the elongate member 350 and the area surrounding the elongate member 350.

The distal retention member 310 of the stent 300 is solid. Said another way, the distal retention member 310 does not include a plurality of beads and/or a plurality of spaces. Having a solid distal retention member 310 can increase the rigidity of the distal retention member 310. Thus, the distal retention member 310 can provide better retention within a kidney of a patient.

The proximal retention member 320 of the stent 300 is also solid. Said another way, the proximal retention member 320 does not include a plurality of beads and/or a plurality of spaces. Having a solid proximal retention member 320 can increase the rigidity of the proximal retention member 320. Thus, the proximal retention member 320 can provide better retention within a bladder of a patient.

FIG. 3 is a cross-sectional view of the stent 200, taken along line X-X in FIG. 2. FIG. 3 shows the plurality of beads 260 coupled together and defining the plurality of spaces 270. As stated above, urine is configured to flow between the plurality of spaces 270 when the stent 200 is disposed within a urinary tract of a patient.

Figure 4:
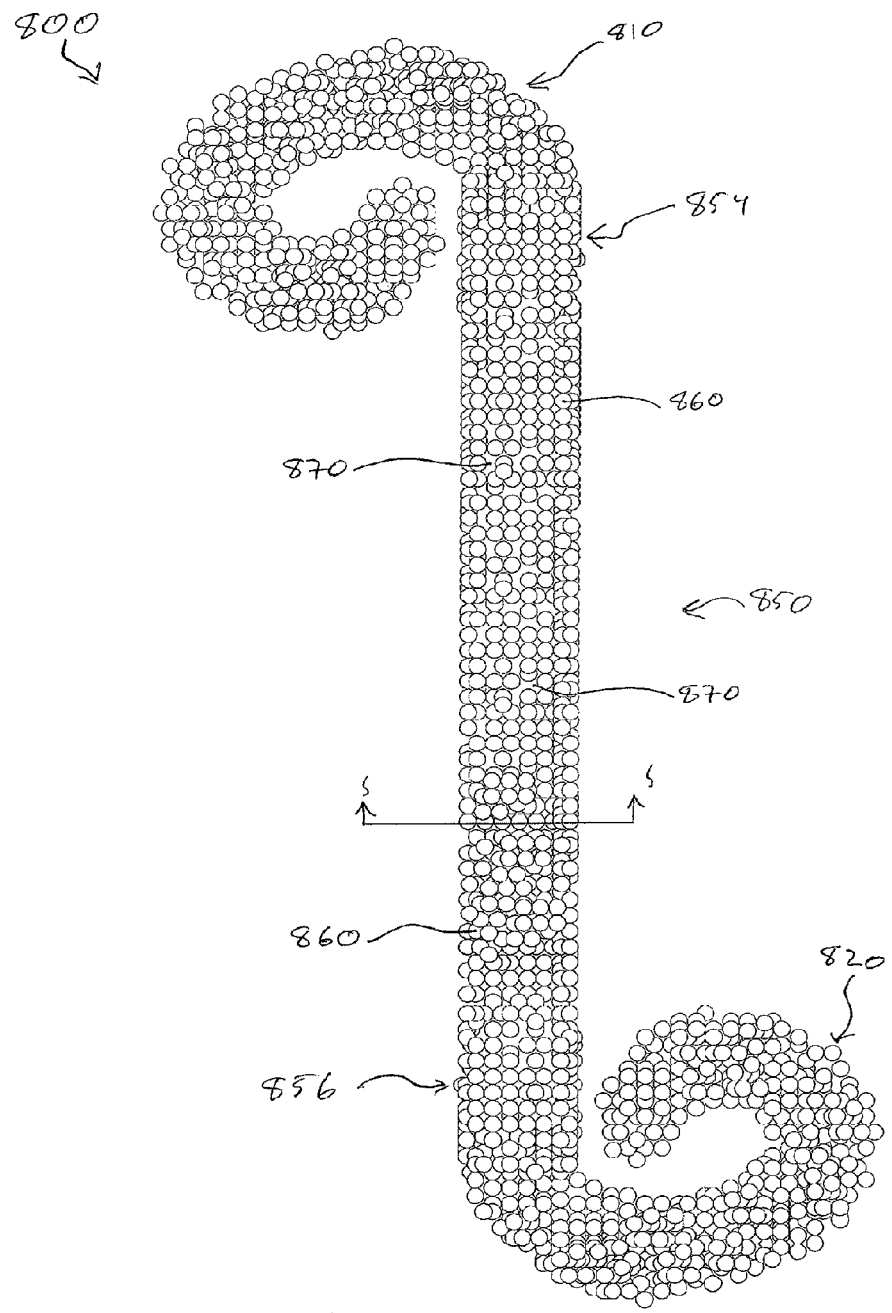
FIG. 4 is a front view of a stent according to an embodiment.
Figure 5:
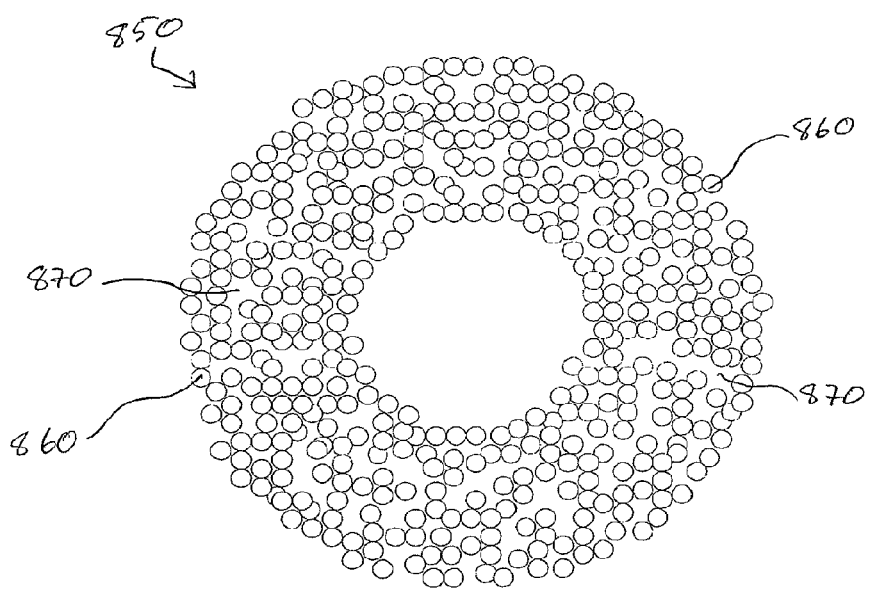
FIG. 5 is a cross-sectional view of the stent shown in FIG. 4, taken along line S-S in FIG. 4.

FIG. 4 is a front view of a stent 800 according to an embodiment. FIG. 5 is a cross-sectional view of the stent 800, taken along line S-S in FIG. 4. The stent 800 is similar to stent 200 and has an elongate member 850, a proximal retention member 820 and a distal-retention member 810. The proximal retention member 820 is coupled to a proximal end portion 856 of the elongate member 850 and the distal retention member 810 is coupled to a distal end portion 854 of the elongate member 850.

The elongate member 850 of the stent 800 includes a plurality of beads 860 that define a plurality of spaces 870. The plurality of beads 860 of the elongate member 850 further define an inner lumen 880 (see e.g., FIG. 5). The plurality of spaces 870 defined by the plurality of beads 860 of the stent 800 are configured to allow fluid to flow from the distal end portion 854 of the elongate member 850 to the proximal end portion 856 of the elongate member 850. The inner lumen 880 defined by the elongate member 850 is configured to allow fluid to flow from the distal end portion 854 of the elongate member 850 to the proximal end portion 856 of the elongate member 850. Because the size of the inner lumen 880 is greater than the size of the plurality of spaces 870, a greater rate of fluid may flow from the kidney to the bladder of the patient when the stent 800 is placed within the urinary tract of a patient. Additionally, the inner lumen 880 is in fluidic communication with the area surrounding the elongate member 850 via the plurality of spaces 870. This allows fluid to flow between the area surrounding the elongate member 850 and the inner lumen 880.

In use, the stent 800 is inserted into the urinary tract of a patient. While the stent 200 can be inserted into the urinary tract using a delivery sheath or the like, because the stent 800 defines an inner lumen 880 the stent 800 can also be inserted into the urinary tract using a guide wire threaded through the inner lumen 880.

The stent 800 is placed within the urinary tract such that the distal retention member 810 is disposed within the kidney of the patient, the proximal retention member 820 is disposed within the bladder of the patient, and the elongate member 850 extends from the kidney of the patient to the bladder of the patient. When the stent 800 is placed within the urinary tract, urine can flow from the kidney, through the inner lumen 880 and/or the plurality of spaces 870 defined by the plurality of beads 860, and into the bladder of the patient.

Figure 7:
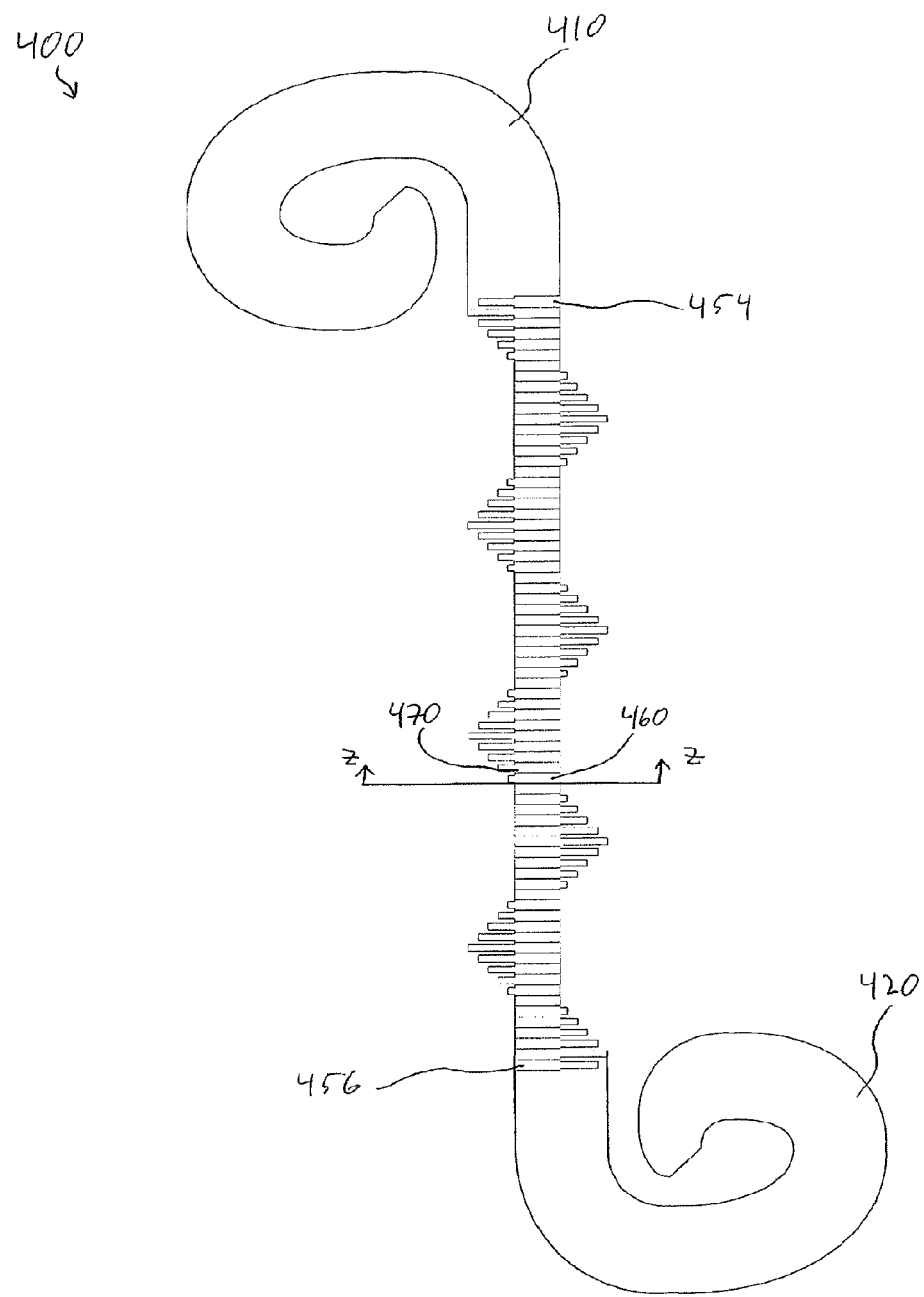
FIG. 7 is a front view of a stent according to an embodiment.
Figure 8:
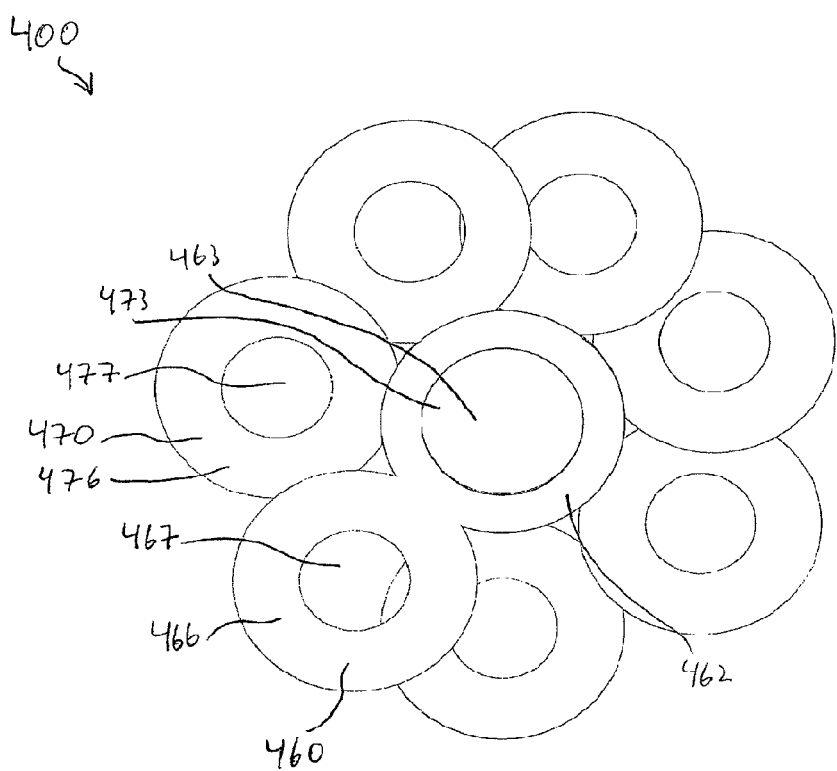
FIG. 8 is a cross-sectional view of the stent shown in FIG. 7, taken along line Z-Z in FIG. 7.

FIGS. 7-8 show a stent 400 according to an embodiment. The stent 400 is similar to the stent 300 and includes an elongate member 450, a proximal retention member 420, and a distal retention member 410. The elongate member 450 of the stent 400 includes a distal end portion 454, a proximal end portion 456 and a plurality of beads.

Figure 9A:
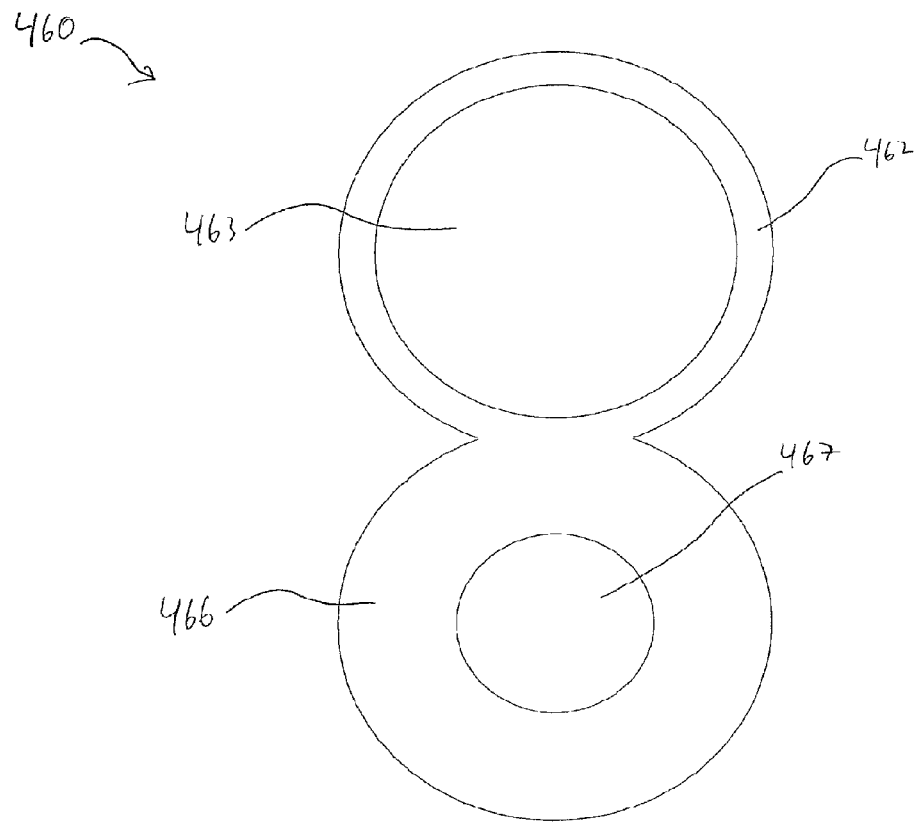
FIG. 9a is a top view of a bead used in the stent shown in FIG. 7.
Figure 9B:
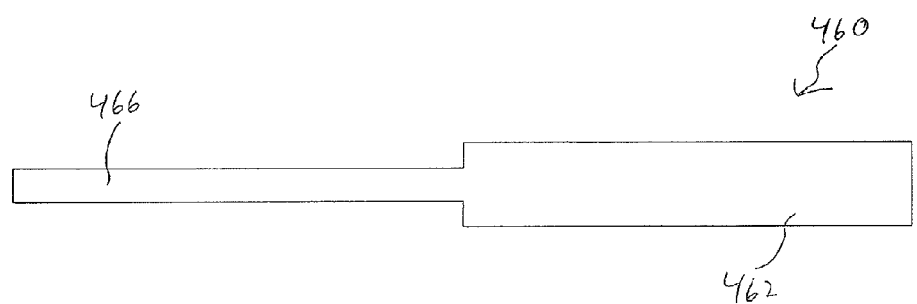
Figure 9C:
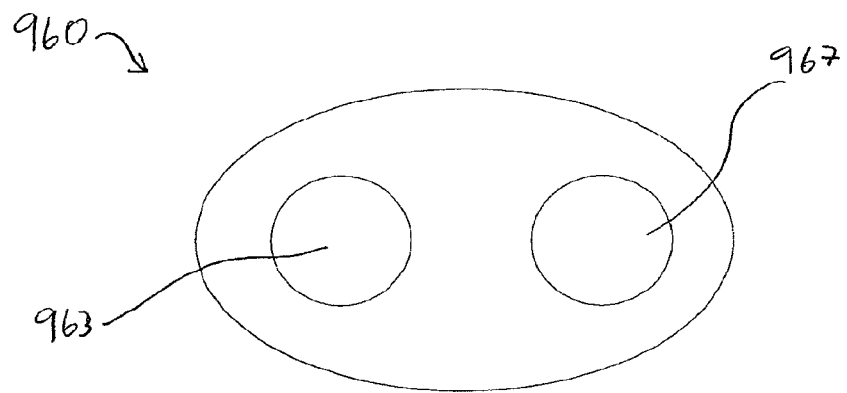
FIG. 9c-e are top views of beads according to other embodiments.

FIGS. 9a-9b show a single bead 460 of the plurality of beads of the stent 400. Each bead 460 of the plurality of beads includes a first portion 462 and a second portion 466. The first portion 462 is substantially circular in shape and defines a lumen 463. The lumen 463 is configured to allow a liquid to flow through it. The lumen 463 defined by the first portion 462 is configured to be aligned with the lumen defined by the first portion of each of the plurality of beads, as described in further detail herein (see e.g., FIG. 8). Further, the first portion 462 of the bead 460 is configured to be coupled to the first portion of each adjacent bead of the plurality of beads, as described in further detail herein.

The second portion 466 of the bead 460 is substantially circular in shape and defines a lumen 467. The lumen 467 defined by the second portion 466 is configured to be offset from the lumen defined by the second portion of each bead of the plurality of beads disposed adjacent the bead 460 when the plurality of beads are stacked together as shown in FIGS. 7 and 8, and as described in further detail herein. Further, the second portion 466 of the bead 460 is configured to be spaced apart from the second portion of each bead disposed adjacent the bead 460 when the plurality of beads are stacked together, as described in further detail herein. As shown in FIG. 9b, the second portion 466 of the bead 460 has a width that is less than a width of the first portion 462 of the bead 460. The first portion 462 of the bead 460 and the second portion 466 of the bead 460 are arranged such that the bead 460 is substantially "figure 8" shaped.

As shown in FIGS. 7 and 8, the plurality of beads are coupled together to form the stent 400. The first portion 462 of a first bead 460 of the plurality of beads is coupled to the first portion 472 of a second bead 470 of the plurality of beads. The second bead 470 of the plurality of beads is substantially similar to the first bead 460 and is disposed adjacent the first bead 460. The lumen 463 defined by the first portion 462 of the first bead 460 is aligned and in fluid communication with the lumen 473 defined by the first portion 472 of the second bead 470.

The second portion 466 of the first bead 460 is offset from the second portion 476 of the second bead 470. Said another way, the lumen 467 defined by the second portion 466 of the first bead 460 is not aligned with the lumen 477 defined by the second portion 476 of the second bead 470. Further, the second portion 466 of the first bead 460 is not in contact with the second portion 476 of the second bead 470. Therefore, the second portion 466 of the first bead 460 and the second portion 476 of the second bead 470 define a space between them. As shown in FIGS. 7 and 8, additional beads are coupled to the first bead 460 and the second bead 470 in the manner described above. In this manner, the stent 400 is formed. In other embodiments, the lumen defined by the second portion of the first bead is partially aligned with the lumen defined by the second portion of the second bead.

The distal retention member 410 of the stent 400 is solid and is coupled to the distal end portion 454 of the elongate member 450. The distal retention member 410 does not include a plurality of beads and/or a plurality of spaces. Having a solid distal retention member 410 can increase the rigidity of the distal retention member 410. Thus, the distal retention member 410 can provide better retention within a kidney of a patient. In other embodiments, the distal retention member of the stent includes a plurality of beads, similar to the bead 460.

The proximal retention member 420 of the stent 400 is solid and is coupled to the proximal end portion 456 of the elongate member 450. The proximal retention member 420 does not include a plurality of beads and/or a plurality of spaces. Having a solid proximal retention member 420 can increase the rigidity of the proximal retention member 420. Thus, the proximal retention member 420 can provide better retention within a bladder of a patient. In other embodiments, the distal retention member of the stent includes a plurality of beads, similar to the bead 460.

In use, the stent 400 is inserted into the urinary tract of a patient. For example, the stent 400 can be inserted into the urinary tract using a delivery sheath, a guide wire, and/or the like. Once disposed within the urinary tract of the patient, urine is configured to flow through the lumens defined by the first portions of the plurality of beads from a kidney to a bladder of the patient. Urine is also configured to flow through the lumens defined by the second portions of the plurality of beads and the spacing between the second portions of the plurality of beads.

In one embodiment, when the stent 400 is disposed within the urinary tract of the patient, the second portion of each of the plurality of beads contacts the ureter of the patient. For example, the second portion 466 of the first bead 460 of the plurality of beads and the second portion 476 of the second bead 470 of the plurality of beads contact the ureter of the patient. In this manner, the stent 400 helps support the ureter of the patient.

In some embodiments, because the second portion of each of the plurality of beads is offset from and does not contact the second portion of adjacent beads, the elongate member 450 minimally contacts the ureter of a patient. This can decrease the irritation and/or discomfort the patient feels when the stent 400 is disposed within the urinary tract of the patient.

In some embodiments, the first portion of each bead has a width that is less than or smaller than the width of the second portion of each bead. Thus, when assembled, the second portion of each bead of the plurality of beads is coupled to the second portion of the beads adjacent each bead and the first portion of each bead of the plurality of beads can be spaced apart from the first portion of the beads adjacent each bead.

In further embodiments, a first portion of one bead has a width that is greater than the width of the second portion of the bead, while a first portion of another bead has a width that is smaller than the width of the second portion of that another bead. In such an embodiment, first portions and/or second portions of adjacent beads may be fused or coupled together. For example, a first portion of a first bead may be coupled to a first portion of a second bead and a second portion of the first bead may be coupled to a second portion of a third bead.

While FIGS. 7-9b show a substantially "figure 8" shaped bead 460, in other embodiments, the bead can be any suitable shape. FIGS. 9c-9e show various beads that can be used to construct a stent similar to the stent 400 described above. For example, FIG. 9c shows an oval shaped bead 960 defining a first lumen 963 and a second lumen 967. The first lumen 963 is configured to allow a liquid, such as urine, to flow through it. The first lumen 963 is configured to be aligned with the first lumen defined by each bead used to construct the stent. In this manner, liquid can flow from a kidney of a patient to a bladder of a patient when the stent is disposed within a ureter of a patient. The second lumen 967 can be offset from the second lumen defined by each bead disposed adjacent the bead 960 when the beads are stacked or coupled together to form the stent.

Figure 9D:
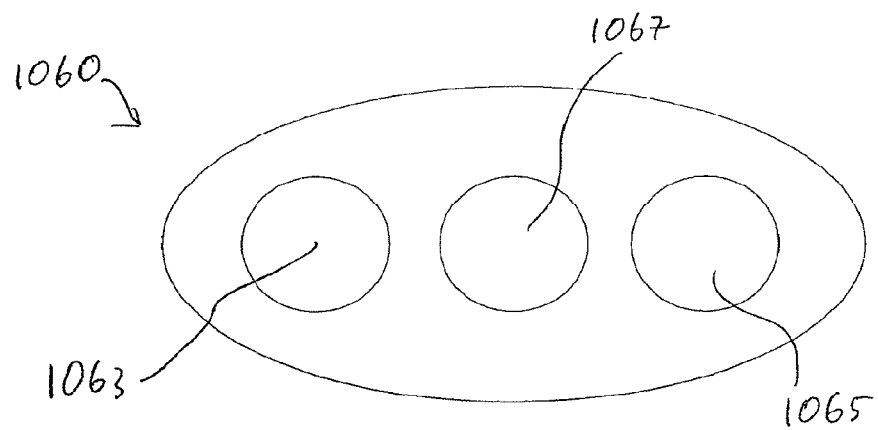

FIG. 9d shows an oval shaped bead 1060 defining a first lumen 1063, a second lumen 1067, and a third lumen 1065. The second lumen 1067 is configured to allow a liquid, such as urine, to flow through it. The second lumen 1067 is configured to be aligned with the second lumen defined by each bead used to construct the stent. In this manner, liquid can flow from a kidney of a patient to a bladder of a patient when the stent is disposed within a ureter of a patient. The first lumen 1063 and the third lumen 1065 can be offset from the first lumen and the third lumen defined by each bead disposed adjacent the bead 1060, respectively, when the beads are stacked together to from the stent. In other embodiments, the first lumen or the third lumen can be aligned with the first lumen or the third lumen defined by each bead used to construct the stent, respectively. In such embodiments, the second lumen can be offset from the second lumen defined by each bead disposed adjacent the bead when the beads are stacked or coupled together to form the stent.

Figure 9E:
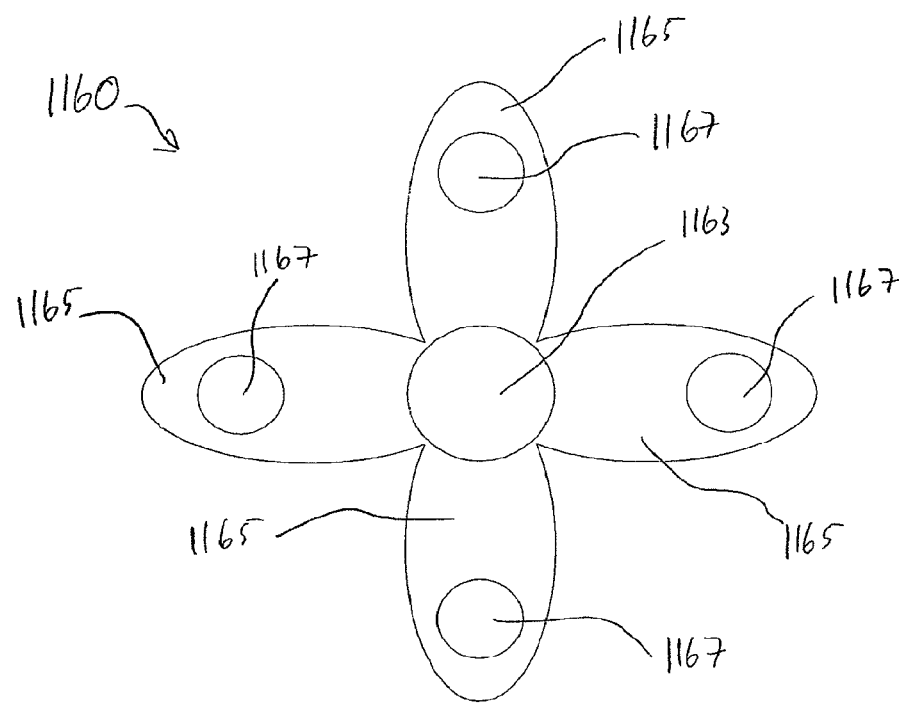

FIG. 9e shows a substantially cross shaped bead 1160 having a plurality of legs 1165 and defining a middle lumen 1163. The each leg of the plurality of legs 1165 defines a lumen 1167. The middle lumen 1163 defined by the bead 1160 is configured to allow liquid, such as urine, to flow through it. In this manner, liquid can flow from a kidney of a patient to a bladder of a patient when the stent is disposed within a ureter of a patient. The middle lumen 1163 is also configured to be aligned with the middle lumen defined by each bead used to construct the stent. The lumens 1167 defined by the plurality of legs 1165 are configured to be offset from the lumens defined by the plurality of legs of each bead disposed adjacent the bead 1160 when the beads are stacked or coupled together to form the stent.

Figure 10:
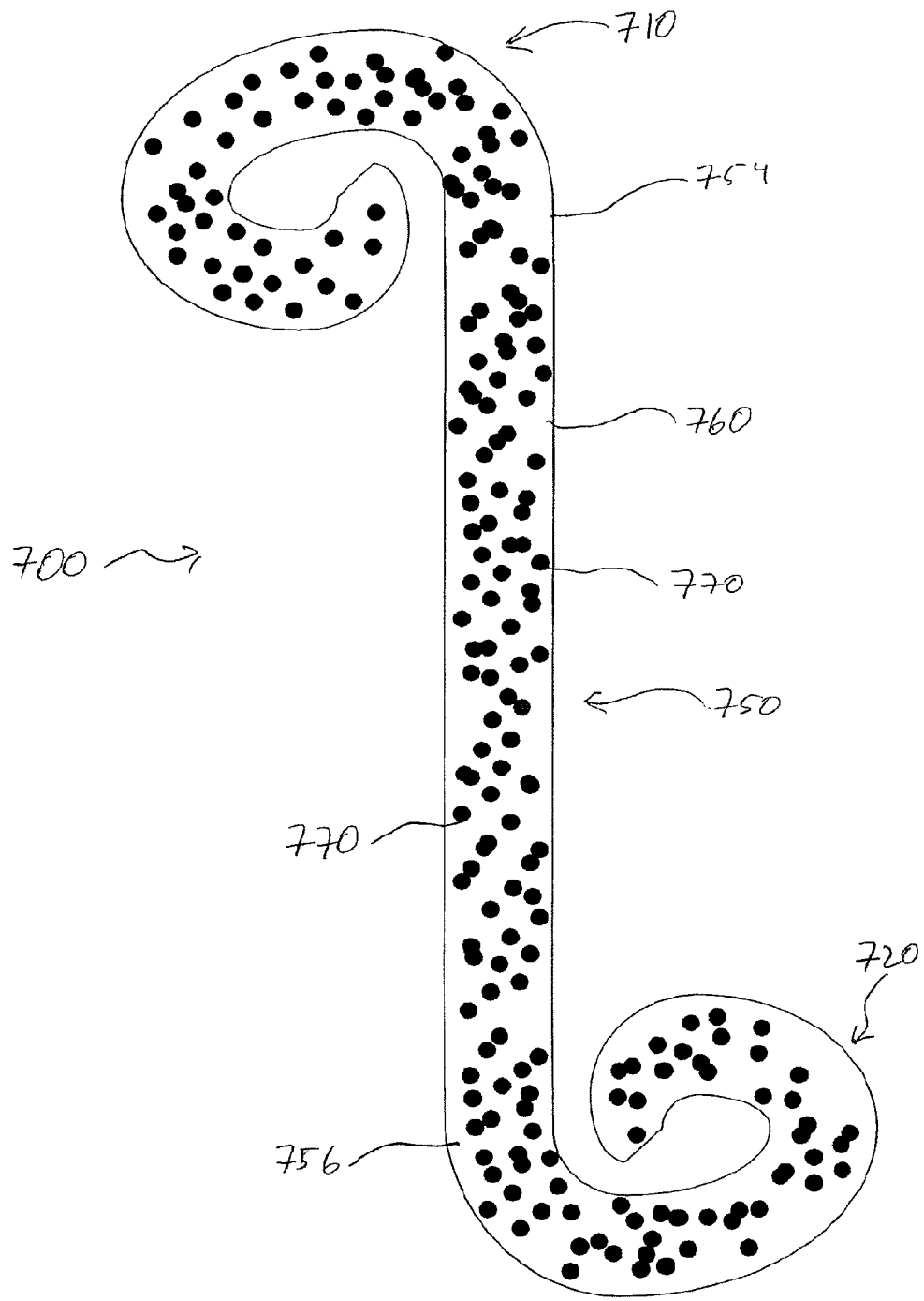
FIG. 10 is a front view of a stent according to an embodiment in a first configuration.
Figure 11:
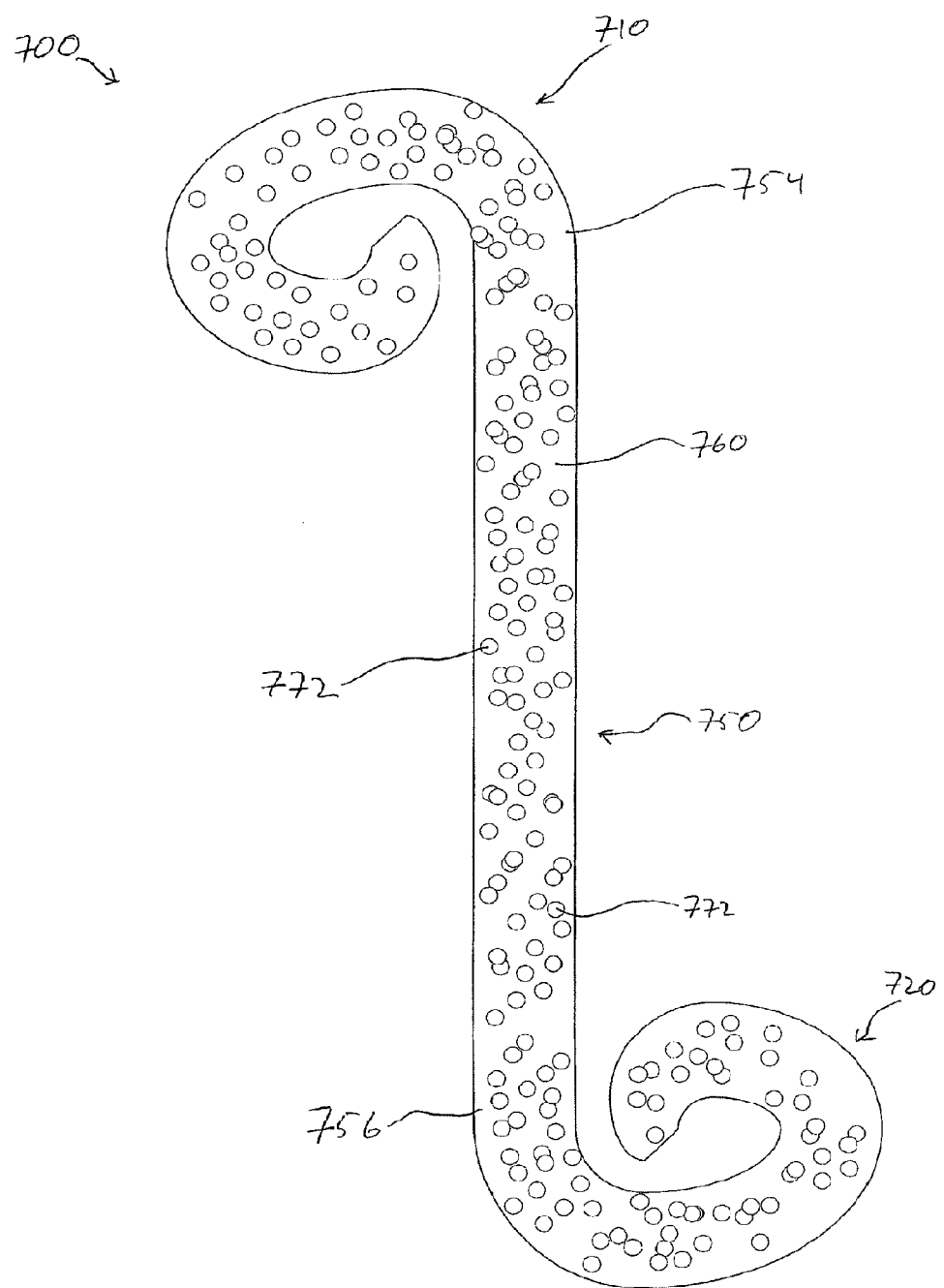
FIG. 11 is a front view of the stent shown in FIG. 10 in a second configuration.

FIGS. 10 and 11 show a stent 700 according to an embodiment. The stent 700 includes a distal retention member 710, a proximal retention member 720 and an elongate member 750. The stent 700 has a first configuration (FIG. 10) and a second configuration (FIG. 11). The elongate member 750 of the stent 700 has a distal end portion 754, and a proximal end portion 756. The elongate member 750 is configured to be disposed within a ureter of a patient and can provide support to the ureter of the patient. In some embodiments, the elongate member defines a lumen through which urine can flow when the elongate member is disposed within a ureter of a patient.

The stent 700, including the distal retention member 710, the proximal retention member 720 and the elongate member 750, is constructed of a first material 760 and a second material 770. As shown in FIG. 10, the second material 770 is interspersed within the first material 760. For example, the second material 770 can be interspersed within the first material 760 in spherical portions. The portions of the second material 770 are nonuniformly interspersed within the first material 760 such that when the second material 770 dissolves, as further described herein, a plurality of spaces 772 are created. The plurality of spaces 772 allow fluid to flow from a distal end portion 754 of the elongate member 750 to a proximal end portion 756 of the elongate member 750. In other embodiments, the portions of the second material have shapes other than spheres. In still other embodiments, the portions of the second material are uniformly spaced apart from each other.

The second material 770 is highly soluble in aqueous solutions. In some embodiments, for example, the second material 770 can be formed of a crystallized salt. The crystallized salt can be inorganic and/or organic salt. For example, the salt can be sodium chloride, sodium acetate and/or sodium citrate. Because the second material 770 is highly soluble in aqueous solutions, the second material 770 is configured to dissolve when the stent 700 is placed within an aqueous solution.

After the second material 770 dissolves, a plurality of spaces 772 are defined by the first material 760. The plurality of spaces 772 are defined or located where the second material 770 was located prior to dissolving. The plurality of spaces 772 cause the stent 700 to be softer than the stent 700 prior to the second material 770 dissolving. The amount the stent 700 softens when placed within an aqueous solution can be varied by varying the amount of second material 770 in the stent 700. The greater the amount of second material 770 included in the stent 700, the softer the stent 700 will become when the second material 770 dissolves. The softness of the stent 700 may also vary with the softness of the first material 760.

The first material 760 can be a thermal elastic polymer such as EVA or Percuflex polymers as sold by Boston Scientific. The first material 760 is configured to remain solid and not dissolve when the second material 770 dissolves.

Prior to being inserted into a body of a patient, the stent 700 is placed within an aqueous solution. This causes the second material 770 to dissolve, leaving the plurality of spaces 772 and moving the stent 700 from its first configuration (FIG. 10) to its second configuration (FIG. 11). When in its second configuration, each space of the plurality of spaces 772 can be in fluid communication with other spaces of the plurality of spaces 772. In this manner, fluid is configured to flow through the plurality of spaces 772 from the distal end portion 754 of the elongate member 750 to the proximal end portion 756 of the elongate member. Additionally, as shown in FIG. 11, the distal retention member 710 and the proximal retention member 720 retain their pigtail shape when the stent 700 is in the second configuration.

In use, the stent 700 is inserted into the urinary tract of a patient. In some embodiments, the stent 700 can be inserted into the urinary tract using a delivery sheath or the like. The stent 700 is placed within the urinary tract such that the distal retention member 710 is disposed within the kidney of the patient, the proximal retention member 720 is disposed within the bladder of the patient, and the elongate member 750 extends from the kidney of the patient to the bladder of the patient. When urine is in the kidney of the patient, the urine can flow through the plurality of spaces 770 defined by the plurality of beads 760 from the distal end portion 754 of the elongate member 750 to the proximal end portion 756 of the elongate member 750 and into the bladder of the patient.

Figure 12:
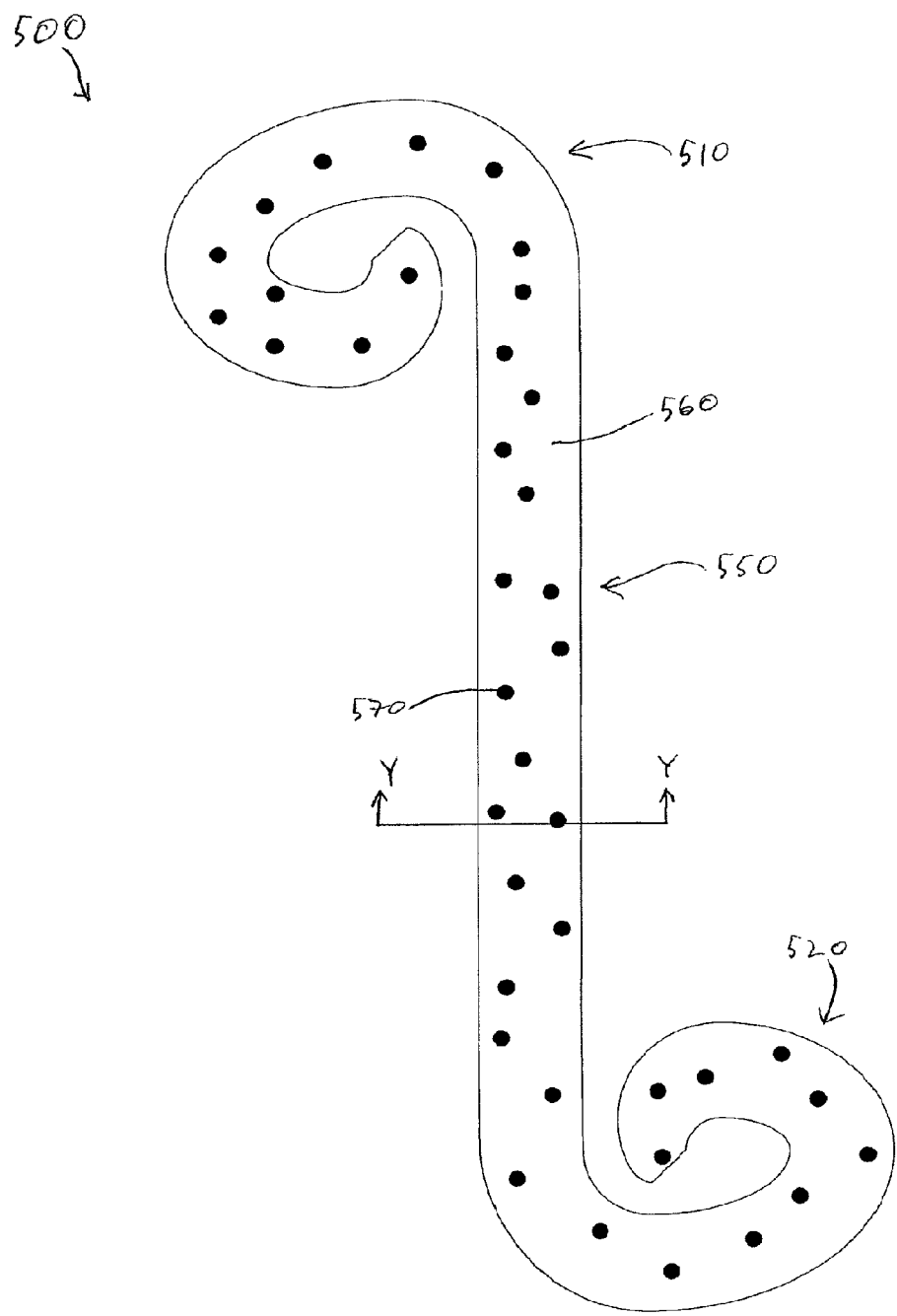
FIG. 12 is a front view of a stent according to an embodiment in a first configuration.
Figure 13:
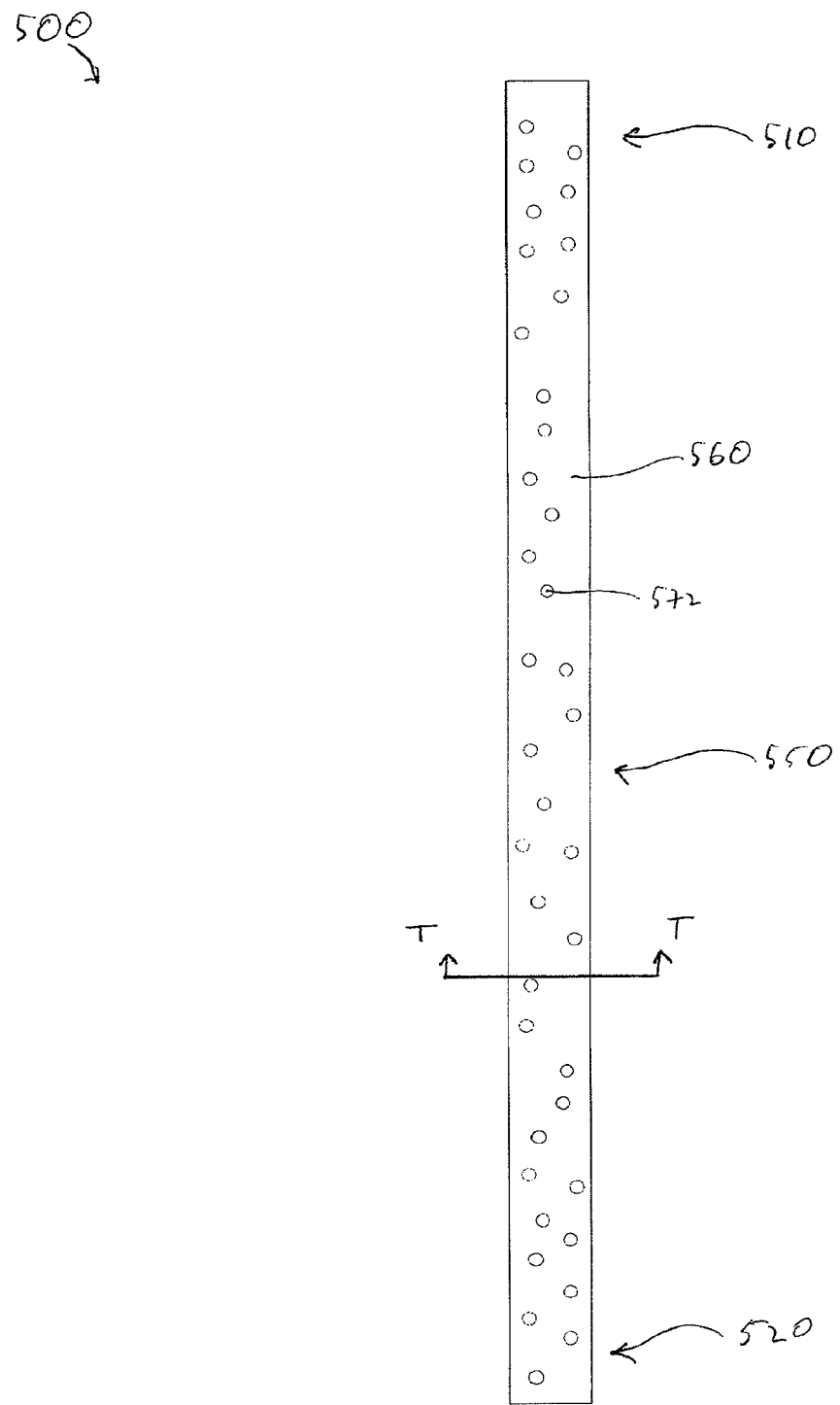
FIG. 13 is a front view of the stent shown in FIG. 12 in a second configuration.
Figure 14:
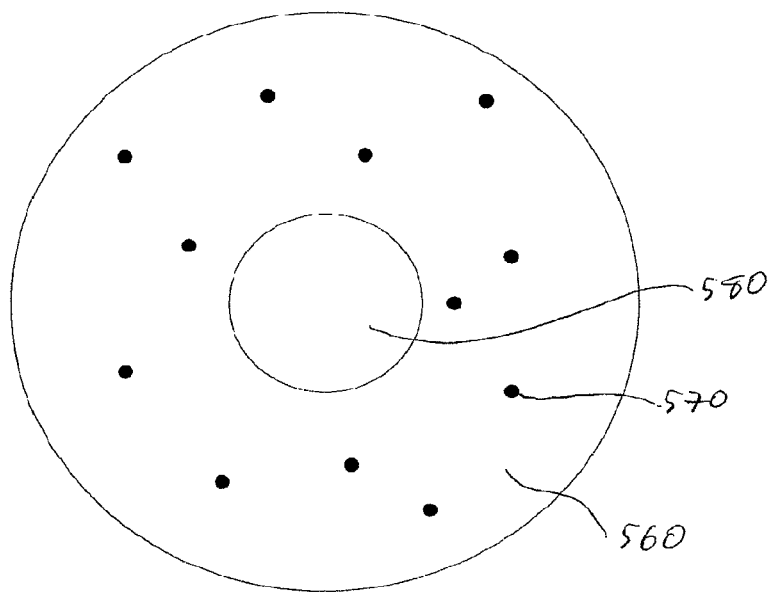
FIG. 14 is a cross-sectional view of the stent shown in FIG. 12 in the first configuration, taken along the line Y-Y in FIG. 12.

FIGS. 12-15 show a stent 500 according to an embodiment. The stent 500 includes a distal retention member 510, a proximal retention member 520 and an elongate member 550. The stent 500 has a first configuration (FIG. 12) and a second configuration (FIG. 13). Similar to the stent 200 described above, the elongate member 550 of the stent 500 is configured to be disposed within a ureter of a patient and can provide support to the ureter of the patient. The elongate member 550 defines a lumen 580 through which urine can flow when the elongate member 550 is disposed within a ureter of a patient.

Figure 15:
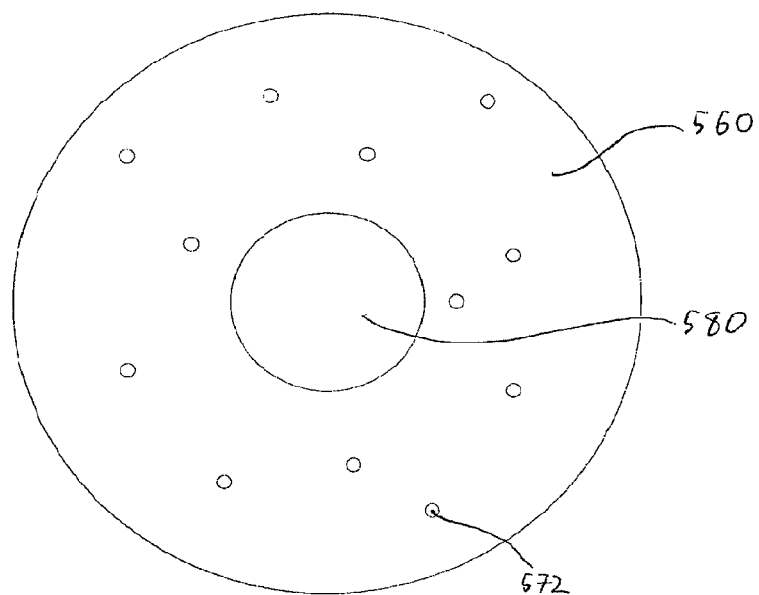
FIG. 15 is a cross-sectional view of the stent shown in FIG. 12 in the second configuration, taken along the line T-T in FIG. 13.

The stent 500, including the distal retention member 510, the proximal retention member 520 and the elongate member 550, is constructed of a first material 560 and a second material 570. As shown in FIGS. 12 and 15, the second material 570 is interspersed within the first material 560. For example, the second material 570 can be interspersed within the first material 560 in spherical portions having diameters of about 1 micron to about 200 microns. The portions of the second material 570 are nonuniformly spaced apart from each other. In other embodiments, the portions of the second material have shapes other than spheres. In still other embodiments, the portions of the second material are uniformly spaced apart from each other.

The second material 570 is highly soluble in aqueous solutions, such as, for example, urine. In some embodiments, for example, the second material 570 is formed of a crystallized salt. The crystallized salt can be inorganic and/or organic salt. For example, the salt can be sodium chloride, sodium acetate and/or sodium citrate. Salts that do not form precipitation with calcium and/or magnesium and/or salts that do not irritate the tissue of a patient, are preferred. In other embodiments, the second material is another suitable material such as glucose, sugar, herbal extracts, and/or the like.

Because the second material 570 is highly soluble in aqueous solutions, the second material 570 is configured to dissolve over a predetermined time period when the stent 500 is disposed within the urinary tract of a patient. In some embodiments, for example, the second material 570 dissolves in a period of between about one and four days. In other embodiments, the second material dissolves in a period of between four and twenty-four hours. In still other embodiments, the second material dissolves in less than four hours. In still other embodiments, the second material takes more than four days to dissolve.

After the second material 570 dissolves, a plurality of spaces 572 are defined by the first material 560. The plurality of spaces 572 are defined or located where the second material 570 was located prior to dissolving. The plurality of spaces 572 cause the stent 500 to be softer than the stent 500 prior to the second material 570 dissolving The first material 560 can be a thermal elastic polymer such as EVA or Percuflex polymers as sold by Boston Scientific. The first material 560 is configured to remain solid when the second material 570 dissolves. The first material 560 does not dissolve when the stent 500 is placed within the urinary tract of a patient.

The stent 500 has a first configuration (FIG. 12) and a second configuration (FIG. 13). Before the second material 570 dissolves, the stent 500 is in the first configuration. When in the first configuration, the stent 500 is substantially rigid. Because the stent 500 is substantially rigid in the first configuration, the stent 500 can easily be placed within a body of a patient. Additionally, the stent 500 maintains its shape when in the first configuration.

When the stent 500 is in the first configuration, the distal retention member 510 has a pigtail shape. The pigtail shape of the distal retention member 510 is configured to help retain a portion of the stent 500 in a kidney of a patient when the stent 500 is placed within a urinary tract of a patient. The distal retention member 510 is configured to prevent the proximal migration of the stent 500 when the stent 500 is in the first configuration. In this manner, the distal retention member 510 is configured to help retain the elongate member 550 in a ureter of a patient, when the stent 500 is in the first configuration.

Similar to the distal retention member 510, when the stent 500 is in the first configuration, the proximal retention member 520 has a pigtail shape. The pigtail shape of the proximal retention member 520 is configured to help retain a portion of the stent 500 in a bladder of a patient when the stent 500 is placed within a urinary tract of a patient. The proximal retention member 520 is configured to prevent the distal migration of the stent 500 when the stent 500 is in the first configuration. In this manner, the proximal retention member 520 is configured to help retain the elongate member 550 in a ureter of a patient, when the stent 500 is in the first configuration.

The stent 500 is inserted into the urinary tract of a patient when in the first configuration. Said another way, the stent 500 is inserted into the urinary tract of the patient prior to the second material 570 dissolving. In some embodiments, the stent 500 can be inserted into the urinary tract using a delivery sheath, a guide wire and/or the like. For example, a guide wire can be inserted through the lumen 580 defined by the elongate member 550. The guide wire can straighten the distal retention member 510 and the proximal retention member 520 to enable insertion of the stent 500 into the body of a patient. Alternatively, a delivery sheath can be disposed around the stent 500 and can be configured to straighten the distal retention member 510 and the proximal retention member 520.

The stent 500 is placed within the urinary tract such that the distal retention member 510 is disposed within the kidney of the patient, the proximal retention member 520 is disposed within the bladder of the patient, and the elongate member 550 extends from the kidney of the patient to the bladder of the patient. Once the guide wire and/or the delivery sheath is removed, the distal retention member 510 and the proximal retention member 520 regain their shape as shown in FIG. 12. When urine is in the kidney of the patient, the urine can flow through the lumen 580 defined by the elongate member 550, from the distal end portion 554 of the elongate member 550 to the proximal end portion 556 of the elongate member 550, and into the bladder of the patient.

The stent 500 moves from the first configuration (FIG. 12) to the second configuration (FIG. 13) when the second material 570 dissolves and creates the plurality of spaces 572 in the stent 500. In the second configuration, the stent 500 becomes soft and the distal retention member 510 and the proximal retention member 520 become flexible and lose their biasing. In some embodiments, the distal retention member 510 and the proximal retention member 520 define axes that are substantially collinear with an axis defined by the elongate member 550 when the stent 500 is in the second configuration.

When the stent 500 is placed within the urinary tract of the patient, the second material 570 is exposed to urine that flows from the kidney of the patient to the bladder of the patient and after a predetermined time, the second material 570 dissolves. Accordingly, the stent 500 moves from the first configuration (FIG. 12) to the second configuration (FIG. 13). As described above, when the stent 500 is in the second configuration, the stent 500 softens and the distal retention member 510 and the proximal retention member 520 become flexible and lose their biasing. When the distal retention member 510 loses its biasing, it no longer retains a portion of the stent 500 within a kidney of a patient. Similarly, when the proximal retention member 520 loses its biasing, it no longer retains a portion of the stent 500 within a bladder of a patient. As such, the stent 500 can be easily removed from the urinary tract of the patient.

In some embodiments, the second material 570 can be configured to maintain acidic urine and/or lower the pH of urine when dissolved within the urine of a patient. Lowering the pH of the urine can reduce the formation of bacterial biofilm and/or prevent encrustation of urine when the stent 500 is disposed within the urinary tract of a patient.

In one embodiment, the stent 500 is manufactured by adding the second material 570, to a base resin consisting of the first material 560. Depending on how soft the stent 500 is to become once the second material 570 dissolves, the amount of second material 570 added to the first material 560 can be varied. The greater the amount of second material 570 in the stent 500, the softer the stent 500 will become after the second material 570 dissolves. Then the stent 500 is formed. The stent 500 can be formed by placing the base resin into a mold and/or the like. Once the stent 500 is formed, it can be inserted into a body of a patient as described above.

In some embodiments, the first material and/or the second material includes a therapeutic agent. The therapeutic agent can be configured to promote wound healing when the stent is disposed adjacent a wound. In some embodiments, the therapeutic agent is configured to dissolve and enter the urine stream when the stent is disposed within the urinary tract of a patient. In this manner, the therapeutic agent promotes wound healing and/or induces other desired effects on a portion of a body of a patient that is not directly in contact with the elongate member. In other embodiments, the first material and/or the second material is configured to generate oxygen when exposed to the urine of a patient.

Figure 16:
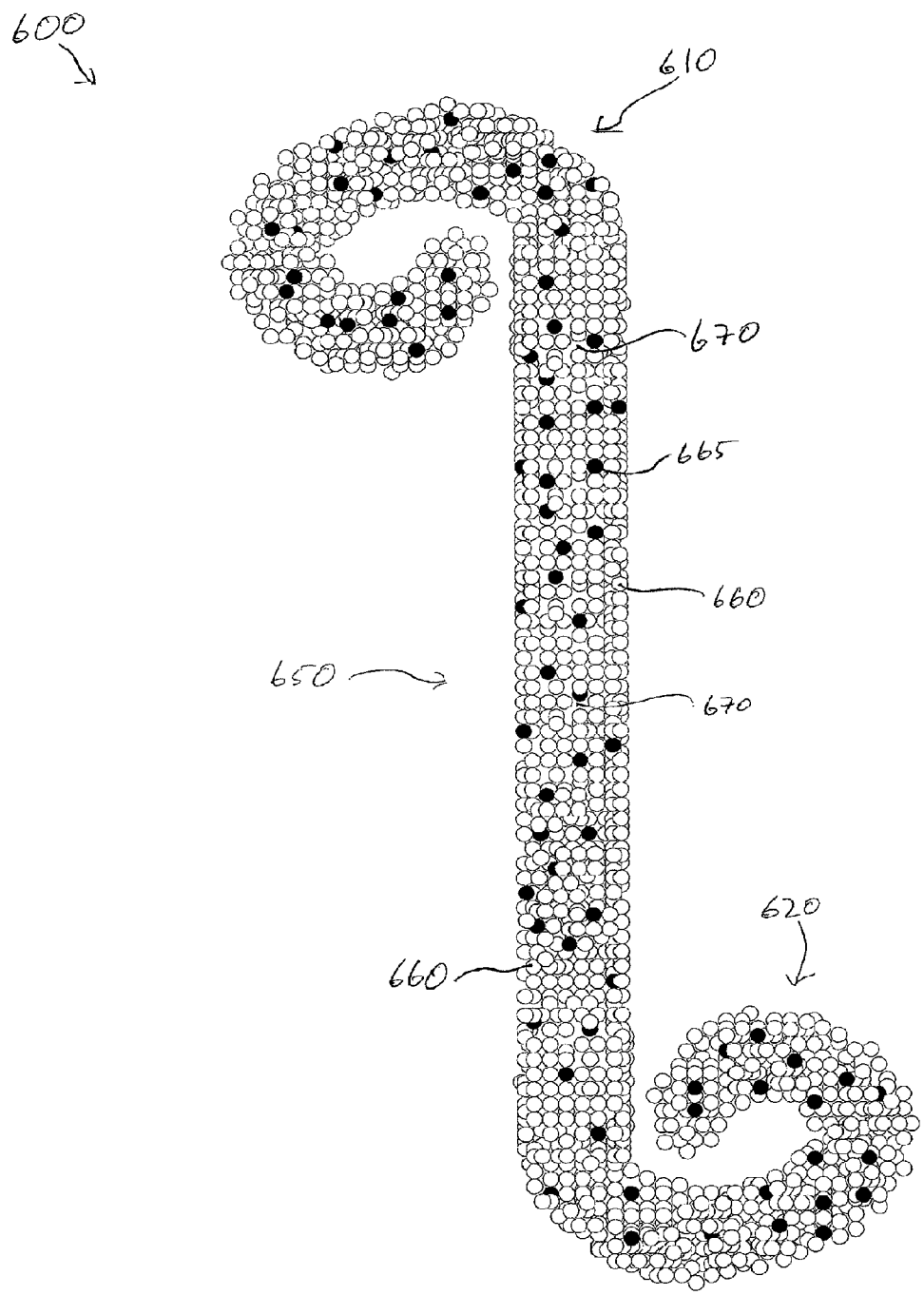
FIG. 16 is a front view of a stent according to an embodiment.

While stent 500 is shown as being solid, FIG. 16 shows a stent 600 according to an embodiment, that is constructed from a plurality of beads of a first material 660 and a plurality of beads of a second material 665. The stent 600 includes a distal retention member 610, a proximal retention member 620 and an elongate member 650. Similar to the stent 500, the stent 600 has a first configuration (FIG. 16) and a second configuration (not shown).

The distal retention member 610 and the proximal retention member 620 are configured to help retain at least a portion of the stent 600 within a kidney of a patient and within a bladder of a patient, respectively, when in the first configuration. The elongate member 650 is configured to be disposed within the ureter of a patient.

The distal retention member 610, the proximal retention member 620 and the elongate member 650 of the stent 600 include a plurality of beads of a first material 660 and a plurality of beads of a second material 665. When the stent 600 is disposed within the urinary tract of a patient, the plurality of beads of the second material 665 are configured to dissolve over a period of time. When the plurality of beads of the second material 665 dissolve, the stent 600 softens and can easily be removed from the body of the patient.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although various embodiments have been described as having particular features and/or combinations of components, other embodiments are possible having a combination of any features and/or components from any of embodiments where appropriate. For example, similar to stent 500, stent 200 can be made of two or more different materials, one of which is configured to dissolve when the stent is placed within a ureter of a patient. Additionally, any of the embodiments described herein can be constructed with solid retention members and/or retention members including beads.

In some embodiments, a stent includes an elongate member and a distal retention member. The elongate member has a first portion, a second portion, and a plurality of beads bonded together. The plurality of beads define a plurality of spaces between the plurality of beads. The plurality of spaces are configured to allow fluid to flow from the first portion of the elongate member to the second portion of the elongate member. The elongate member is configured to be disposed within a ureter of a patient. The distal retention member is configured help maintain a portion of the stent within a kidney of the patient.

In some embodiments, the elongate member defines a lumen extending from the first portion of the elongate member to the second portion of the elongate member. In some embodiments, the plurality of beads are thermal elastic plastic beads. In some embodiments, the plurality of beads are fused together. In some embodiments, the distal retention member includes a plurality of beads. In some embodiments, the distal retention member is unitarily formed.

In some embodiments, the stent includes a proximal retention member configured to help maintain a portion of the stent within a bladder of the patient. In some embodiments, the proximal retention member includes a plurality of beads. In some embodiments, the proximal retention member is unitarily formed.

In some embodiments, the plurality of beads are substantially spherical. In some embodiments, at least one bead of the plurality of beads includes a therapeutic agent.

In some embodiments, the elongate member defines a longitudinal axis and the plurality of spaces are configured to allow fluid to flow in a direction substantially normal to the longitudinal axis. In some embodiments, the plurality of spaces are configured to allow fluid to flow in a direction substantially normal to the longitudinal axis and in a direction substantially parallel to the longitudinal axis.

In some embodiments, a stent includes an elongate member having a distal end portion, a proximal end portion, and a plurality of beads. The elongate member defines a longitudinal axis. Each bead of the plurality of beads has a first portion and a second portion. The first portion of each of the plurality of beads defines a lumen. The lumens of the first portions of each of the plurality of beads are substantially aligned along the longitudinal axis such that the lumen defined by the first portion of the first bead of the plurality of beads is in fluid communication with the lumen defined by the first portion of a second bead of the plurality of beads. The second portion of the first bead of the plurality of beads is offset from the second portion of the second bead of the plurality of beads.

In some embodiments, the second portion of the first bead of the plurality of beads defines a lumen. The second portion of the second bead of the plurality of beads defines a lumen. The lumen defined by the second portion of the second bead is offset from the lumen defined by the second portion of the first bead.

In some embodiments, the plurality of beads are substantially figure eight shaped. In some embodiments, at least one bead of the plurality of beads includes a therapeutic agent.

In some embodiments, the stent includes a proximal retention member configured to help maintain a portion of the stent within a bladder of a patient. In some embodiments, the proximal retention member includes a plurality of beads. In some embodiments, the proximal retention member is unitarily formed.

In some embodiments, the stent includes a distal retention member configured to help maintain a portion of the stent within a kidney of a patient. In some embodiments, the distal retention member includes a plurality of beads. In some embodiments, the distal retention member is unitarily formed.

In some embodiments, the second portion of the first bead of the plurality of beads is coupled to the second portion of the second bead of the plurality of beads.

In some embodiments, the second portion of the first plurality of beads does not contact the second portion of the second bead of the plurality of beads. The first bead is adjacent the second bead.

In some embodiments, the first portion of the first bead of the plurality of beads is coupled to the first portion of the second bead of the plurality of beads.

In some embodiments, the first portion of the first bead of the plurality of beads does not contact the first portion of the second bead of the plurality of beads. The first bead is adjacent the second bead.

In some embodiments, a stent includes an elongate member configured to extend from a kidney to a bladder of a patent. The elongate member includes a first material and a second material. The second material is formulated to dissolve when the stent is disposed within a urinary tract of the patient for a predetermined amount of time. The stent is softer after the second material dissolves.

In some embodiments, the second material is crystallized salt. In some embodiments, the second material has a high solubility in aqueous solutions. In some embodiments, the second material is formulated to lower the pH of urine when dissolved within the urinary tract of the patient. In some embodiments, the second material ix formulated to promote wound healing when dissolved adjacent to a wound of a patient.

In some embodiments, the stent includes a distal retention member having the first material and the second material. The distal retention member is configured to move from a first configuration to a second configuration when the stent is disposed within the urinary tract of the patient for a predetermined amount of time. The distal retention member is configured to help maintain a portion of the stent within the kidney of the patient when in the first configured. The distal retention member configured to allow the stent to migrate from the kidney of the patient to the bladder of the patient when in the second configuration.

In some embodiments, the first material is a thermal elastic polymer. In some embodiments, the second material is interspersed within the first material in portions having diameters between 1-200 microns.

In some embodiments, the predetermined amount of time is between one and seven days. In some embodiments, the second material is interspersed within the first material before dissolving.

What is claimed is:

1. A stent comprising:
   an elongate member having a distal end portion, a proximal end portion and a plurality of beads, the elongate member defining a longitudinal axis, each bead of the plurality of beads has a first portion and a second portion, the first portion of each of the plurality of beads defines a lumen, the second portion the first bead of the plurality of beads defines a lumen and the second portion of the second bead of the plurality of beads defines a lumen, the lumen defined by the second portion of the second bead is offset from the lumen defined by the second portion of the first bead.

2. The stent of claim 1, wherein the plurality of beads are substantially figure eight shaped.

3. The stent of claim 1, further comprising:
a proximal retention member configured to help maintain a portion of the stent within a bladder of a patient, the proximal retention member including a plurality of beads.

4. The stent of claim 1, wherein the second portion of the first bead of the plurality of beads does not contact the second portion of the second bead of the plurality of beads, the first bead being adjacent the second bead.

5. The stent of claim 1, wherein the first portion of the first bead of the plurality of beads is coupled to the first portion of the second bead of the plurality of beads.

6. The stent of claim 1, wherein the first portion of the first bead of the plurality of beads does not contact the first portion of the second bead of the plurality of beads, the first bead being adjacent the second bead.

7. A stent comprising:
an elongate member configured to extend from a kidney to a bladder of a patient, the elongate member including a first material and a second material, the second material formulated to dissolve when the stent is disposed within a urinary tract of the patient for a predetermined amount of time, the stent being softer after the second material dissolves, the second material being a crystallized salt.

8. The stent of claim 7, wherein the second material has a high solubility in aqueous solutions.

9. The stent of claim 7, wherein the second material is formulated to lower the pH of urine when dissolved within the urinary tract of the patient.

10. The stent of claim 7, wherein the second material is formulated to promote wound healing when dissolved adjacent to a wound of the patient.

11. The stent of claim 7, further comprising:
a distal retention member including the first material and the second material, the distal retention member configured to move from a first configuration to a second configuration when the stent is disposed within the urinary tract of the patient for the predetermined amount of time,
the distal retention member configured to help maintain a portion of the stent within the kidney of the patient when in the first configuration,
the distal retention member configured to allow the stent migrate from the kidney of the patient to the bladder of the patient when in the second configuration.

12. The stent of claim 7, wherein the second material is interspersed within the first material before dissolving.

* * * * *